United States Patent
Phan et al.

(10) Patent No.: US 6,812,216 B2
(45) Date of Patent: Nov. 2, 2004

(54) 11-C-SUBSTITUTED DERIVATIVES OF CLARITHROMYCIN

(75) Inventors: Ly Tam Phan, Malden, MA (US); Jay Judson Farmer, New Haven, CT (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 72 days.

(21) Appl. No.: 10/178,991

(22) Filed: Jun. 25, 2002

(65) Prior Publication Data

US 2004/0006027 A1 Jan. 8, 2004

(51) Int. Cl.⁷ .......................... A61K 31/70; C07H 17/08
(52) U.S. Cl. ........................... 514/29; 536/7.2; 536/7.3; 536/7.4
(58) Field of Search .................. 514/29; 536/7.2, 536/7.3, 7.4

(56) References Cited

U.S. PATENT DOCUMENTS

| | | | |
|---|---|---|---|
| 4,847,242 A | 7/1989 | Davies et al. | |
| 4,990,602 A | 2/1991 | Morimoto et al. | 536/7.4 |
| 5,403,923 A | 4/1995 | Kashimura et al. | 536/7.4 |
| 5,444,051 A | 8/1995 | Agouridas et al. | 514/29 |
| 2003/0125266 A1 | 7/2003 | Chu et al. | |

FOREIGN PATENT DOCUMENTS

| | | |
|---|---|---|
| WO | PCT/US97/05871 | 7/1998 |
| WO | WO 03/004509 | 1/2003 |
| WO | WO 03/047600 | 6/2003 |

*Primary Examiner*—Elli Peselev
(74) *Attorney, Agent, or Firm*—Jason D. Ferrone; Gaetano D. Maccarone

(57) ABSTRACT

There are described 11-C-substituted derivatives of clarithromycin and pharmaceutically acceptable compositions comprising a therapeutically effective amount of a compound of the invention in combination with a pharmaceutically acceptable carrier. Also described is a method for treating bacterial infections by administering to an animal a pharmaceutical composition containing a therapeutically-effective amount of a compound of the invention, and processes for the preparation of such compounds.

12 Claims, No Drawings

11-C-SUBSTITUTED DERIVATIVES OF CLARITHROMYCIN

CROSS-REFERENCE TO RELATED APPLICATIONS

This application is related to commonly assigned U.S. patent application, Ser. No. 10/179,590, filed on even date herewith.

TECHNICAL FIELD

The present invention relates to novel macrolides having antibacterial activity and useful in the treatment and prevention of bacterial infections. More particularly, the invention relates to a novel class of 11-C-substituted erythromycin derivatives, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin and clarithromycin.

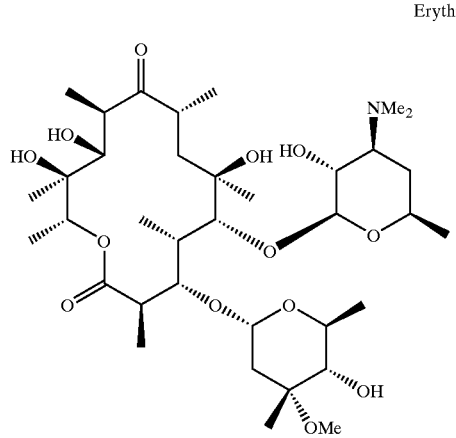

Erythromycin

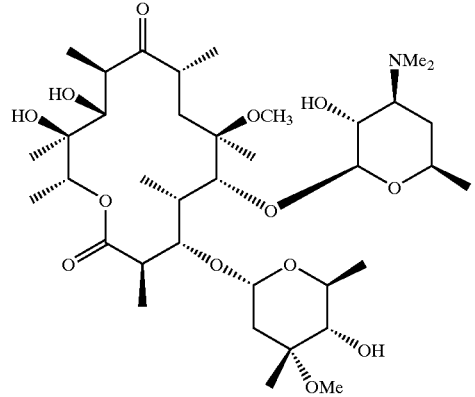

Clarithromycin

The search for macrolides active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides a novel class of 11-C-substituted derivatives of clarithromycin possessing antibacterial activity toward Gram positive and Gram negative bacteria as well as macrolide Gram positives.

In one embodiment, the present invention provides compounds represented by formulae I, II, III or IV, as well as the pharmaceutically acceptable salts, esters and prodrugs thereof.

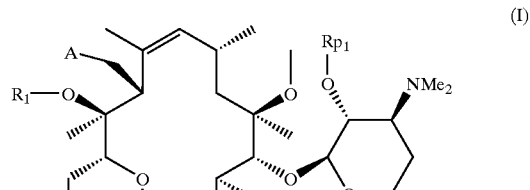

(I)

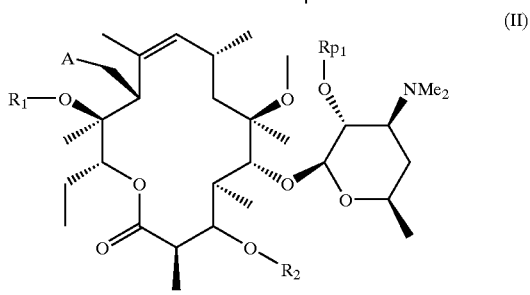

(II)

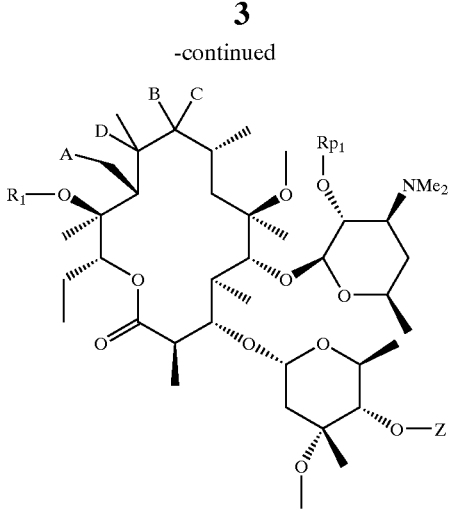

(III)

(IV)

In formulae I–IV above,

A is selected from the group consisting of
(1) $C_1$–$C_6$-alkyl, $C_2$–$C_6$-alkenyl or $C_2$–$C_6$-alkynyl, optionally substituted with one or more substituents selected from the group consisting of:
  i. halogen;
  ii. aryl;
  iii. substituted aryl;
  iv. heterocyclic;
  V. substituted heterocyclic;
  vi. —O—$R_5$, where $R_5$ is selected from the group consisting of:
    a. hydrogen;
    b. aryl;
    c. substituted aryl;
    d. heterocyclic; and
    e. substituted heterocyclic;
  vii. —O—$C_1$–$C_6$-alkyl-$R_5$, where $R_5$ is as previously defined;
  viii. —O—$C_2$–$C_6$-alkenyl-$R_5$, where $R_5$ is as previously defined;
  ix. —O—$C_2$–$C_6$-alkynyl-$R_5$, where $R_5$ is as previously defined; and
  x. —$NR_6R_7$, where $R_6$ and $R_7$ are each independently selected from the group consisting of:
    a. hydrogen;
    b. $C_1$–$C_6$-alkyl, optionally substituted with one or more substituents selected from the group consisting of:
      (I) halogen;
      (II) aryl;
      (III) substituted aryl;
      (IV) heterocyclic; and
      (V) substituted heterocyclic;
    c. $C_2$–$C_6$-alkenyl, optionally substituted with one or more substituents selected from the group consisting of:
      (I) halogen;
      (II) aryl;
      (III) substituted aryl;
      (IV) heterocyclic; and
      (V) substituted heterocyclic;
    d. $C_2$–$C_6$-alkynyl, optionally substituted with one or more substituents selected from the group consisting of:
      (I) halogen;
      (II) aryl;
      (III) substituted aryl;
      (IV) heterocyclic; and
      (V) substituted heterocyclic, or
    e. $R_6$ $R_7$ taken with the nitrogen atom to which they are connected form a 3- to 7-membered ring which may optionally contain one or more functions selected from the group consisting of:
      (I) —O—;
      (II) —NH—;
      (III) —N($C_1$–$C_6$-alkyl)-;
      (IV) —N(aryl)-;
      (V) —N(heteroaryl)-;
      (VI) —S—;
      (VII) —S(O)—;
      (VIII) —S(O)$_2$—; and
      (IX) —C(O)—;
(2) —C(O)—$R_5$, where $R_5$ is as previously defined;
(3) —C(O)—$C_1$–$C_6$-alkyl-$R_5$, where $R_5$ is as previously defined;
(4) —C(O)—$C_2$–$C_6$-alkenyl-$R_5$, where $R_5$ is as previously defined;
(5) —C(O)—$C_2$–$C_6$-alkynyl-$R_5$, where $R_5$ is as previously defined;
(6) $C_1$–$C_6$-alkyl-M-$R_5$, where M is —OC(O)—, —OC(O)O—, —OC(O)$NR_6$—, —C(O)$NR_6$—, —$NR_6$C(O)—, —$NR_6$C(O)O—, —$NR_6$C(O)$NR_7$—, —$NR_6$C(NH)$NR_7$— or S(O)$_n$—, where n=0, 1 or 2, and where $R_5$, $R_6$, $R_7$ are as previously defined;
(7) —$C_2$–$C_6$-alkenyl-M—$R_5$, where M and $R_5$ are as previously defined; and
(8) —$C_2$–$C_6$-alkynyl-M—$R_5$, where M and $R_5$ are as previously defined;

B, C, and D may be present singly or in combination and are independently selected from the group consisting of:
(1) hydrogen;
(2) halogen;
(3) $C_1$–$C_6$-alkyl;
(4) aryl;
(5) substituted aryl;
(6) heteroaryl;
(7) substituted heteroaryl;
(8) O—$R_5$ where $R_5$ is as previously defined;
(9) B and C taken together are =O;
(10) B and C taken together are =N—O—$R_5$, where $R_5$ is as previously defined;
(11) B and C taken together are =N—N—$R_6R_7$, where $R_6$ and $R_7$ are as previously defined;
(12) B and D taken together are —O—;
(13) B and D taken together are —S—;
(14) B and D taken together are —N($R_6$)—, where $R_6$ is as previously defined; and
(15) B and D taken together with the carbon atoms to which they are attached form a 4- to 8-membered ring which may optionally contain one or more functions selected from the group consisting of:
  i. —O—;
  ii. —NH—;
  iii. —N($C_1$–$C_6$-alkyl)-;
  iv. —N(aryl)-;
  v. —N(heteroaryl)-;
  vi. —S—;
  vii. —S(O)—;
  viii. —S(O)$_2$—; and
  ix. —C(O)—;

$R_1$ is selected from the group consisting of:
  (1) hydrogen;
  (2) $R_3$, where $R_3$ is $C_1$–$C_6$-alkyl, $C_2$–$C_6$-alkenyl or $C_2$–$C_6$-alkynyl, optionally substituted with one or more substituents selected from the group consisting of:
    i. halogen;
    ii. aryl;
    iii. substituted-aryl;
    iv. heteroaryl;
    v. substituted-heteroaryl;
    vi. —O—$C_1$–$C_6$-alkyl-$R_5$, where $R_5$ is as previously defined; and
    vii. —N—$R_6R_7$, where $R_6$ and $R_7$ are as previously defined;
  (3) —C(O)—$R_4$, where $R_4$ is hydrogen or $R_3$, where $R_3$ is as previously defined;
  (4) —C(O)O—$R_3$, where $R_3$ is as previously defined; and
  (5) —C(O)N—$R_6R_7$, where $R_6$ and $R_7$ are as previously defined;

$R_2$ is selected from the group consisting of:
  (1) a hydroxy protecting group;
  (2) $R_5$, where $R_5$ is as previously defined;
  (3) —X—Y—$R_5$, where X is —C(O), —C(O)O—, —C(O)N$R_6$—, or absent, and Y is $C_1$–$C_6$-alkyl or absent, where $R_5$ and $R_6$ are as previously defined; and
  (4) $C_1$–$C_6$-alkyl, $C_2$–$C_6$-alkenyl or $C_2$–$C_6$-alkynyl optionally substituted with one or more substituents selected from the group consisting of:
    i. halogen;
    ii. aryl;
    iii. substituted-aryl;
    iv. heteroaryl;
    v. substituted-heteroaryl;
    vi. —O—$R_5$ where $R_5$, is as previously defined;
    vii. —O—$C_1$–$C_6$-alkyl-$R_5$, where $R_5$ is as previously defined;
    viii. —O—$C_2$–$C_6$-alkenyl-$R_5$, where $R_5$ is as previously defined;
    ix. —O—$C_2$–$C_6$-alkynyl-$R_5$, where $R_5$ is as previously defined; and
    x. —N—$R_6R_7$, where $R_6$ and $R_7$ are as previously defined;

$Rp_1$ is hydrogen or a hydroxy protecting group; and
Z is selected from the group consisting of:
  (1) hydrogen;
  (2) a hydroxy protecting group; and
  (3) —X—$R_3$, where X and $R_3$ are as previously defined.

In other embodiments, the present invention provides processes for preparing the compounds represented by formulae I–IV, compositions containing such compounds and methods for using the same.

DETAILED DESCRIPTION OF THE INVENTION

A first embodiment of the invention is a compound represented by formula I as described above, or a pharmaceutically acceptable salt, ester or prodrug thereof.

A second embodiment of the invention is a compound represented by formula II as described above, or a pharmaceutically acceptable salt, ester or prodrug thereof.

A third embodiment of the invention is a compound represented by formula III as described above, or a pharmaceutically acceptable salt, ester or prodrug thereof.

A fourth embodiment of the invention is a compound represented by formula IV as described above, or a pharmaceutically acceptable salt, ester or prodrug thereof.

Other preferred embodiments of the invention are: compounds of formula I where $R_1$ and Z are each hydrogen and A and $Rp_1$ are as previously defined; compounds of formula II where $R_1$ is hydrogen and A, $R_2$ and $Rp_1$ are as previously defined; compounds of formula III where $R_1$ and Z are each hydrogen and A, B, C, D and $Rp_1$ are as previously defined; and compounds of formula IV where $R_1$ is hydrogen and A, B, C, D, $R_2$ and $Rp_1$ are as previously defined.

Representative compounds of the invention are those selected from the group consisting of:
Compound of formula I: A=CHO, $R_1$=H, Z=Ac and $Rp_1$=H;
Compound of formula I: A=$CH_2$OH, $R_1$=H, Z=Ac and $Rp_1$=H;
Compound of formula I: A=$CH_2$OCO-[3-quinolyl], $R_1$=H, Z=Ac and $Rp_1$=H;
Compound of formula I: A=$CH_2$OCO-[4-quinolyl], $R_1$=H, Z=Ac and $Rp_1$=H;
Compound of formula I: A=CH=CH-phenyl, $R_1$=H, Z=Ac and $Rp_1$=H;
Compound of formula I: A=$CH_2$NH-benzyl, $R_1$=H, Z=Ac and $Rp_1$=H;
Compound of formula I: A=$CH_2$NH-allyl, $R_1$=H, Z=Ac and $Rp_1$=H;
Compound of formula II: A=CHO, $R_1$=H, $R_2$=H and $Rp_1$=H;
Compound of formula II: A=CHO, $R_1$=H, $R_2$=benzoyl and $Rp_1$=H;
Compound of formula II: A=$CH_2$OH, $R_1$=H, $R_2$=H and $Rp_1$=H;
Compound of formula II: A=$CH_2$OCO-[3-quinolyl], $R_1$=H, $R_2$=H and $Rp_1$=H;
Compound of formula II: A=$CH_2$OCO-[3-quinolyl], $R_1$=H, $R_2$=benzoyl and $Rp_1$=H;
Compound of formula II: A=$CH_2$OCO-[4-quinolyl], $R_1$=H, $R_2$=H and $Rp_1$=H;
Compound of formula II: A=CH=CH-phenyl, $R_1$=H, $R_2$=H and $Rp_1$=H;
Compound of formula II: A=$CH_2$NH-benzyl, $R_1$=H, $R_2$=H and $Rp_1$=H;
Compound of formula II: A=$CH_2$NH-benzyl, $R_1$=H, $R_2$=benzoyl and $Rp_1$=H;
Compound of formula II: A=$CH_2$NH-allyl, $R_1$=H, $R_2$=H and $Rp_1$=H;
Compound of formula III: A=CHO, B=H, C=H, D=H, $R_1$=H, Z=Ac and $Rp_1$=H;
Compound of formula III: A=CHO, B and D taken together =—O—, C=H, $R_1$=H, Z=Ac and $Rp_1$=H;
Compound of formula III: A=CHO, B and C taken together are =O, D=H, $R_1$=H, Z=Ac and $Rp_1$=H;
Compound of formula III: A=CHO, B=OH, D=OH, C=H, $R_1$=H, Z=Ac and $Rp_1$=H;
Compound of formula III: A=$CH_2$OH, B=H, C=H, D=H, $R_1$=H, Z=Ac and $Rp_1$=H;

Compound of formula III: A=CH$_2$OH, B and D taken together are —O—, C=H, R$_1$=H, Z=Ac and Rp$_1$=H;

Compound of formula III: A=CH$_2$OH, B and C taken together are =O, D=H, R$_1$=H, Z=Ac and Rp$_1$=H;

Compound of formula III: A=CH$_2$OH, B=OH, D=OH, C=H, R$_1$=H, Z=Ac and Rp$_1$=H;

Compound of formula III: A=CH$_2$OCO-[3-quinolyl], B=H, C=H, D=H, R$_1$=H, Z=Ac and Rp$_1$=H;

Compound of formula III: A=CH$_2$OCO-[3-quinolyl], B and D taken together =—O—, C=H, R$_1$=H, Z=Ac and Rp$_1$=H;

Compound of formula III: A=CH$_2$OCO-[3-quinolyl], B and C taken together are =O, D=H, R$_1$=H, Z=Ac and Rp$_1$=H;

Compound of formula III: A=CH$_2$OCO-[3-quinolyl], B=OH, D=OH, C=H, R$_1$=H, Z=Ac and Rp$_1$=H;

Compound of formula III: A=CH$_2$OCO-[4-quinolyl], B=H, C=H, D=H, R$_1$=H, Z=Ac and Rp$_1$=H;

Compound of formula III: A=CH$_2$OCO-[4-quinolyl], B and D taken together =—O—, C=H, R$_1$=H, Z=Ac and Rp$_1$=H;

Compound of formula III: A=CH$_2$OCO-[4-quinolyl], B and C taken together are =O, D=H, R$_1$=H, Z=Ac and Rp$_1$=H;

Compound of formula III: A=CH$_2$OCO-[4-quinolyl], B=OH, D=OH, C=H, R$_1$=H, Z=Ac and Rp$_1$=H;

Compound of formula III: A=CH=CH-phenyl, B=H, C=H, D=H, R$_1$=H, Z=Ac and Rp$_1$=H;

Compound of formula III: A=CH$_2$NH-benzyl, B=H, C=H, D=H, R$_1$=H, Z=Ac and Rp$_1$=H;

Compound of formula III: A=CH$_2$NH-benzyl, B and D taken together =—O—, C=H, R$_1$=H, Z=Ac and Rp$_1$=H;

Compound of formula III: A=CH$_2$NH-benzyl, B and C taken together are =O, D=H, R$_1$=H, Z=Ac and Rp$_1$=H;

Compound of formula III: A=CH$_2$NH-benzyl, B=OH, D=OH, C=H, R$_1$=H, Z=Ac and Rp$_1$=H;

Compound of formula III: A=CH$_2$NH-allyl, B=H, C=H, D=H, R$_1$=H, Z=Ac and Rp$_1$=H;

Compound of formula III: A=CH$_2$NH-allyl, B and D taken together =—O—, C=H, R$_1$=H, Z=Ac and Rp$_1$=H;

Compound of formula III: A=CH$_2$NH-allyl, B and C taken together are =O, D=H, R$_1$=H, Z=Ac and Rp$_1$=H;

Compound of formula III: A=CH$_2$NH-allyl, B=OH, D=OH, C=H, R$_1$=H, Z=Ac and Rp$_1$=H;

Compound of formula IV: A=CHO, B=H, C=H, D=H, R$_1$=H, R$_2$=H and Rp$_1$=H;

Compound of formula IV: A=CHO, B and D taken together =—O—, C=H, R$_1$=H, R$_2$=H and Rp$_1$=H;

Compound of formula IV: A=CHO, B and C taken together are =O, D=H, R$_1$=H, R$_2$=H and Rp$_1$=H;

Compound of formula IV: A=CHO, B=OH, D=OH, C=H, R$_1$=H, R$_2$=H and Rp$_1$=H;

Compound of formula IV: A=CH$_2$OH, B=H, C=H, D=H, R$_1$=H, R$_2$=H and Rp$_1$=H;

Compound of formula IV: A=CH$_2$OH, B and D taken together =—O—, C=H, R$_1$=H, R$_2$=H and Rp$_1$=H;

Compound of formula IV: A=CH$_2$OH, B and C taken together are =O, D=H, R$_1$=H, R$_2$=H and Rp$_1$=H;

Compound of formula IV: A=CH$_2$OH, B=OH, D=OH, C=H, R$_1$=H, R$_2$=H and Rp$_1$=H;

Compound of formula IV: A=CH$_2$OCO-[3-quinolyl], B=H, C=H, D=H, R$_1$=H, R$_2$=H and Rp$_1$=H;

Compound of formula IV: A=CH$_2$OCO-[3-quinolyl], B and D taken together =—O—, C=H, R$_1$=H, R$_2$=H and Rp$_1$=H;

Compound of formula IV: A=CH$_2$OCO-[3-quinolyl], B and C taken together are =O, D=H, R1=H, R$_2$=H and Rp$_1$=H;

Compound of formula IV: A=CH$_2$OCO-[3-quinolyl], B=OH, D=OH, C=H, R$_1$=H, R$_2$=H and Rp$_1$=H;

Compound of Formula IV: A=CH$_2$OCO-[4-quinolyl], B=H, C=H, D=H, R$_1$=H, R$_2$=H and Rp$_1$=H;

Compound of Formula IV: A=CH$_2$OCO-[4-quinolyl], B and D taken together =—O—, C=H, R$_1$=H, R$_2$=H and Rp$_1$=H;

Compound of Formula IV: A=CH$_2$OCO-[4-quinolyl], B and C taken together are =O, D=H, R$_1$=H, R$_2$=H and Rp$_1$=H;

Compound of Formula IV: A=CH$_2$OCO-[4-quinolyl], B=OH, D=OH, C=H, R$_1$=H, R$_2$=H and Rp$_1$=H;

Compound of formula IV: A=CH=CH-phenyl, B=H, C=H, D=H, R$_1$=H, R$_2$=H and Rp$_1$=H;

Compound of Formula IV: A=CH$_2$NH-benzyl, B=H, C=H, D=H, R$_1$=H, R$_2$=H and Rp$_1$=H;

Compound of Formula IV: A=CH$_2$NH-benzyl, B and D taken together =—O—, C=H, R$_1$=H, R$_2$=H and Rp$_1$=H;

Compound of Formula IV: A=CH$_2$NH-benzyl, B and C taken together are =O, D=H, R$_1$=H, R$_2$=H and Rp$_1$=H;

Compound of Formula IV: A=CH$_2$NH-benzyl, B=OH, C=OH, D=H, R$_1$=H, R$_2$=H and Rp$_1$=H;

Compound of Formula IV: A=CH$_2$NH-allyl, B=H, C=H, D=H, R$_1$=H, R$_2$=H and Rp$_1$=H;

Compound of Formula IV: A=CH$_2$NH-allyl, B and D taken together =—O—, C=H, R$_1$=H, R$_2$=H and Rp$_1$=H;

Compound of Formula IV: A=CH$_2$NH-allyl, B and C taken together are =O, D=H, R$_1$=H, R$_2$=H and Rp$_1$=H; and Compound of Formula IV: A=CH$_2$NH-allyl, B=OH, D=OH, C=H, R$_1$=H, R$_2$=H and Rp$_1$=H.

Definitions

The terms "C$_1$–C$_3$ alkyl," "C$_1$–C$_6$ alkyl" or "C$_1$–C$_{12}$ alkyl," as used herein, refer to saturated, straight- or branched-chain hydrocarbon radicals containing between one and three, one and twelve, or one and six carbon atoms, respectively. Examples of C$_1$–C$_3$ alkyl radicals include methyl, ethyl, propyl and isopropyl radicals; examples of C$_1$–C$_6$ alkyl radicals include, but are not limited to, methyl, ethyl, propyl, isopropyl, n-butyl, tert-butyl, neopentyl and n-hexyl radicals; and examples of C$_1$–C$_{12}$ alkyl radicals include, but are not limited to, ethyl, propyl, isopropyl, n-hexyl, octyl, decyl, dodecyl radicals.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The terms "C$_2$–C$_{12}$ alkynyl" or "C$_2$–C$_6$ alkynyl," as used herein, denote a monovalent group derived from a hydrocarbon moiety containing from two to twelve or two to six carbon atoms having at least one carbon-carbon triple bond by the removal of two hydrogen atoms. Representative alkynyl groups include, but are not limited to, for example, ethynyl, 1-propynyl, 1-butynyl, and the like.

The terms "halo" and "halogen," as used herein, refer to an atom selected from fluorine, chlorine, bromine and iodine.

The term "haloalkyl" denotes an alkyl group, as defined above, having one, or more halogen atoms attached thereto, and is exemplified by such groups as chloromethyl, bromoethyl, trifluoromethyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like. Aryl groups (including bicyclic aryl groups) can be unsubstituted or substituted with one, two or three substituents independently selected from lower alkyl, substituted lower alkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "substituted aryl," as used herein, refers to an aryl group, as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH-$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "$C_3$–$C_{12}$-cycloalkyl" denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl.

The term "heterocycloalkyl," as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic", as used herein, refers to heterocycloalkyl and heteroaryl. The term "substituted heterocyclic", as used herein, refers to substituted heterocycloalkyl and substituted heteroalkyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of the formula —CHO.

The term "carboxy," as used herein, refers to a group of the formula —COOH.

The term "carboxamide," as used herein, refers to a group of the formula —C(O)NH($C_1$–$C_{12}$ alkyl) or —C(O)N($C_1$–$C_{12}$ alkyl)($C_1$–$C_{12}$ alkyl).

"Hydroxy protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf. for example, T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-butyldimethylsilyl, tert-butyldiphenylsilyl, acyl substituted with an aromatic group and the like.

The term "protected hydroxy" refers to a hydroxy group protected with a hydroxy protecting group, as defined above, including benzoyl, acetyl, trimethylsilyl, triethylsilyl, methoxymethyl groups, for example.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986.

The term "protic solvent" or "protogenic solvent" as used herein, refers to a solvent that tends to provide protons, such as an alcohol, for example, methanol, ethanol, propanol, isopropanol, butanol, t-butanol, water and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems, Vol. 14 of the ACS Symposium Series, and in Edward B. Roche, ed., "Bioreversible Carriers in Drug Design", American Pharmaceutical Association and Pergamon Press, 1987, both of which are incorporated herein by reference.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 µg/ml to about 0.03 µg/ml. The diluted compounds (2 µl/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 µl/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The pharmaceutical compositions of this invention can be administered to fish by blending them in the fish feed to be administered orally or may be dissolved in water in which sick fish are placed to swim around ( a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Abbreviations

Abbreviations which may be used in the descriptions of the schemes and the examples that follow are: Ac for acetyl; AcOOH for peroxyacetic acid; AIBN for azobisisobutyronitrile; BHT for 2,6-di-tert-butyl-4-methylphenol, Bn for benzyl; Bz for benzoyl; Boc for tert-butoxycarbonyl; BSA for bis-trimethylsilyl acetarnide, t-BuOOH for tertiary-butyl hydroperoxide, $Bu_3SnH$ for tributyltin hydride; CAMHB for cation adjusted Mueller-Hinton broth, CDI for carbonyldiimidazole; DBA for dibenzylidene acetone; DBU for 1,8-diazabicyclo[5.4.0]undec-7-ene; DCC for dicyclohexylcarbodiimide, DEAD for diethylazodicarboxylate; DIBAL-H for diisobutylaluminum hydride, DMAP for 4-N,N-dimethylamino-pyridine; DME for 1,2-dimethoxyethane, DMF for dimethyl formamide; DMSO for dimethylsulfoxide; DPPA for diphenylphosphoryl azide; DPPB for diphenylphosphino butane; EtOAc for ethyl acetate; HMDS for hexamethyldisilazane; KHMDS for potassium bis(trimethylsilyl)amide; LAH for lithium aluminum hydride, LDA for lithium diisopropyl amide; m-CPBA for 3-chloroperoxybenzoic acid, MeOH for methanol; MOM for methoxymethyl; NaHMDS for sodium bis (trimethylsilyl)amide; NMO for N-methylmorpholine N-oxide; Ph for phenyl; Red-Al for sodium bis-(2-methoxyethoxy)aluminum hydride, RT for room temperature; TBAF for tetrabutylammonium fluoride; TBS for tert-butyl dimethylsilyl; TEA for triethylamine; TFA for trifluoroacetic acid; THF for tetrahydrofuran; TMS for trimethyl silyl; and TPP for triphenylphosphine Synthetic Methods The compounds and processes of the present invention will be better understood in connection with the following synthetic schemes that are illustrative of the methods by which the compounds of the invention may be prepared. The groups A, B, C, D, $R_2$, $Rp_1$, and Z are as defined previously, unless otherwise noted below.

Scheme 1
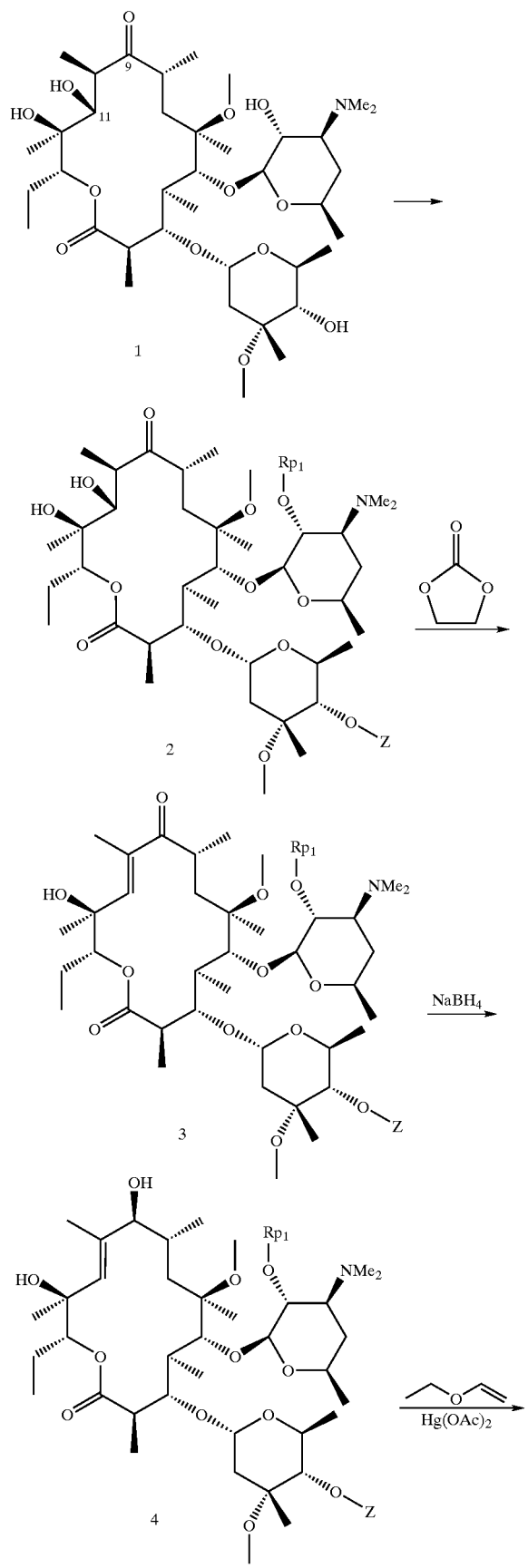
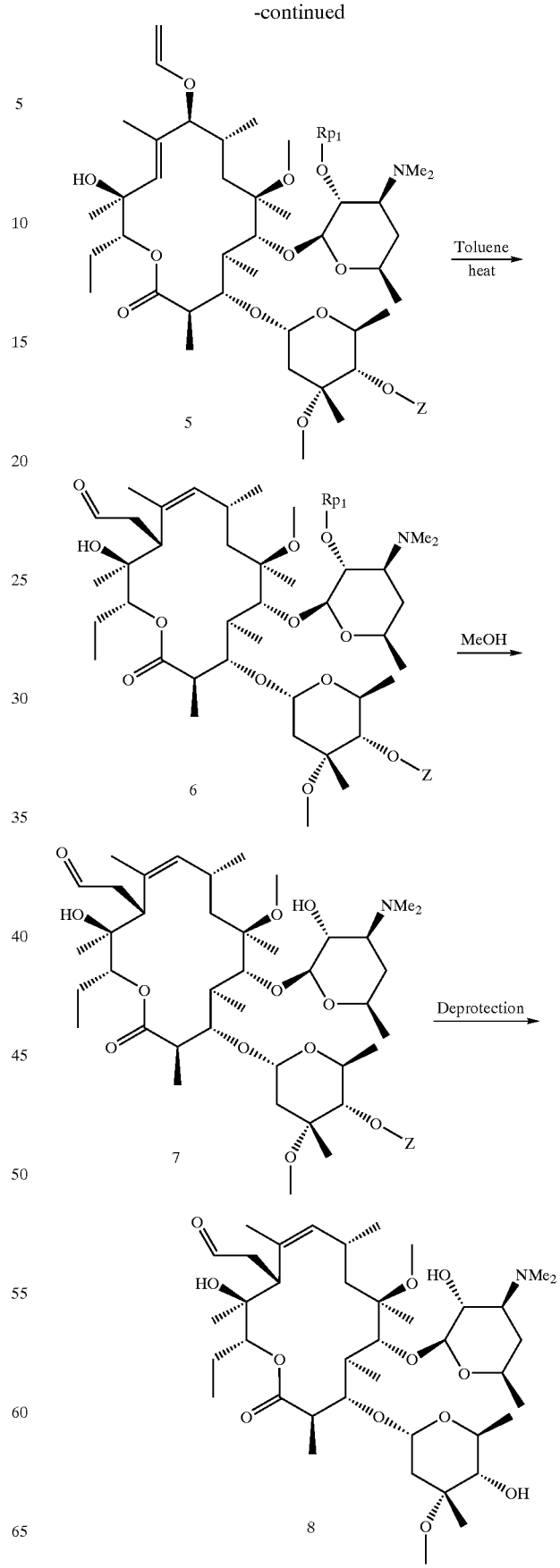

One process of the present invention for the preparations of compounds of formula I is as shown in Scheme 1. According to this synthetic scheme, the preparation of the compounds of formula I includes the step of protecting Clarithromycin (compound 1 of Scheme 1) with an acid anhydride, acid chloride or a silylating reagent such as silyl chloride, HMDS, BSA and the like in an aprotic solvent such as methylene chloride, THF, chloroform, DMF, acetonitrile or the like at a temperature from about 0° C. to about 50° C. for 3–72 hours to provide compound 2. Compound 2 is treated with ethylene carbonate, either as a neat mixture or in an aprotic solvent at room temperature to about 150° C. to provide compound 3. Alternatively, compound 2 is treated with a sulfonic acid chloride or sulfonic acid anhydride in the presence of TEA, pyridine or the like in an aprotic solvent at a temperature of from about 0° C. to about 50° C. to provide the corresponding 11-O-sulfonate ester which is eliminated in a separate step by treatment with a base such as DBU, DMAP, KOt-Bu, or the like at from room temperature to about 100° C. to provide compound 3. Compound 3 further reacts with a reducing agent such as sodium borohydride, sodium triacetoxy borohydride, or the like in a protic solvent such as methanol, ethanol, isopropanol, or the like, or mixtures thereof, with an aprotic solvent such as THF, DME, or the like at from about −20° C. to about 50° C., to provide compound 4. Alternatively, compound 3 is treated with DIBAL-H, LAH, RedAl or the like in an aprotic solvent at from about −80° C. to about room temperature to provide compound 4. Compound 4 is alkylated selectively at the 9 oxygen by treatment with a vinyl ether such as ethyl vinyl ether, or butyl vinyl ether in the presence of a mercury (II) salt, either as a neat mixture or in an aprotic solvent, at from room temperature to about 100° C. to afford compound 5. Compound 5 is thermolyzed in an aprotic solvent such as toluene, xylenes, or decahydronaphthalene at a temperature of from about 80° C. to about 200° C. for 3 to 72 hours, to afford the Claisen rearrangement product 6. Compound 6 is treated with methanol at from about 0° C. to about 60° C. to remove the $Rp_1$ protecting group at the 2' position to form compound 7. Compound 7 is deprotected to form compound 8. When Z is a silyl protecting group, the deprotection process includes, for example, but is not limited to, acid hydrolysis with dilute aqueous acid (0.1–2 N) such as hydrochloric acid, hydrofluoric acid, sulfuric acid, trifluoroacetic acid, acetic acid or the like, optionally in an organic solvent such as acetone, acetonitrile, methanol, ethanol or the like, or combinations thereof, or TBAF or the like; When Z is an ester protecting group, the deprotection process includes, for example, but is not limited to, base hydrolysis with an alkaline hydroxide aqueous solution, optionally in an organic solvent such as THF, methanol, acetonitrile or the like, at from about room temperature to 70° C. for 1–24 hours or other like conditions. Compound 8 may be further derivatized at the 4"-hydroxy position as described in Antimicrob. Agents Chemother. 1989, vol 33, page 78–81 or European Patent 895999.

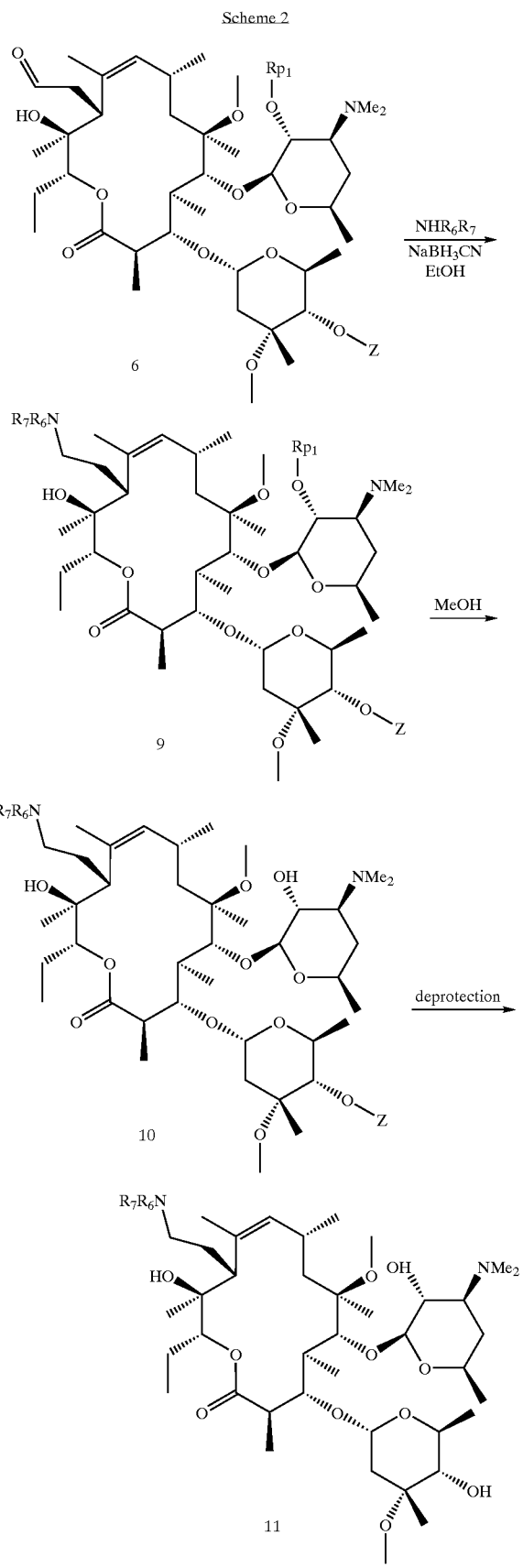

Scheme 2

In another process of the present invention, for the preparation of the compounds of formula I (as shown in Scheme 2), compound 6 from Scheme 1 is reacted further by reductive amination methods with primary or secondary amines in the presence of sodium cyanoborohydride or similar reducing agents, in a protic solvent such as methanol, ethanol, isopropanol or the like to afford compound 9, where $R_6$ and $R_7$ are as defined previously. Compound 9 is treated with methanol as described in Scheme 1 to form compound 10. Compound 10 is then deprotected to provide compound 11 as described in Scheme 1.

Scheme 3

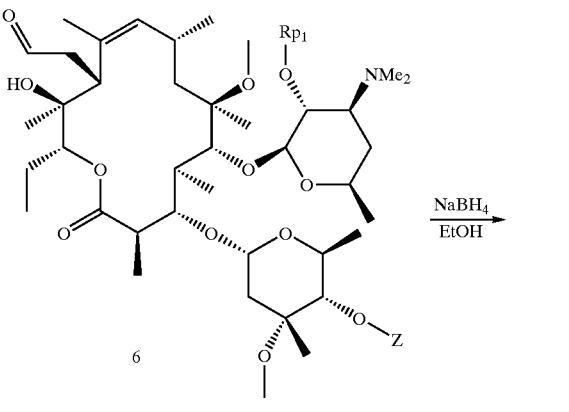

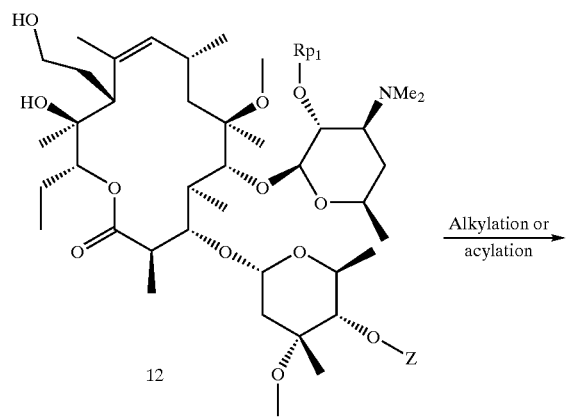

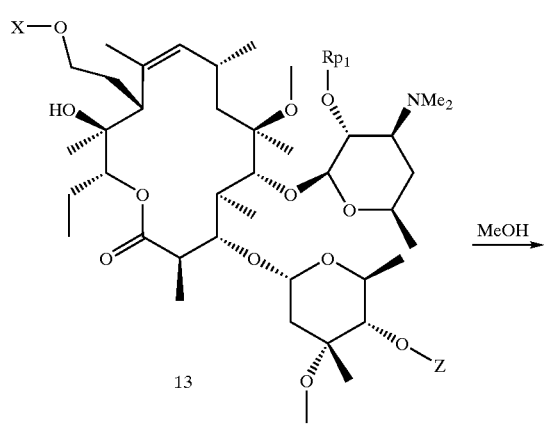

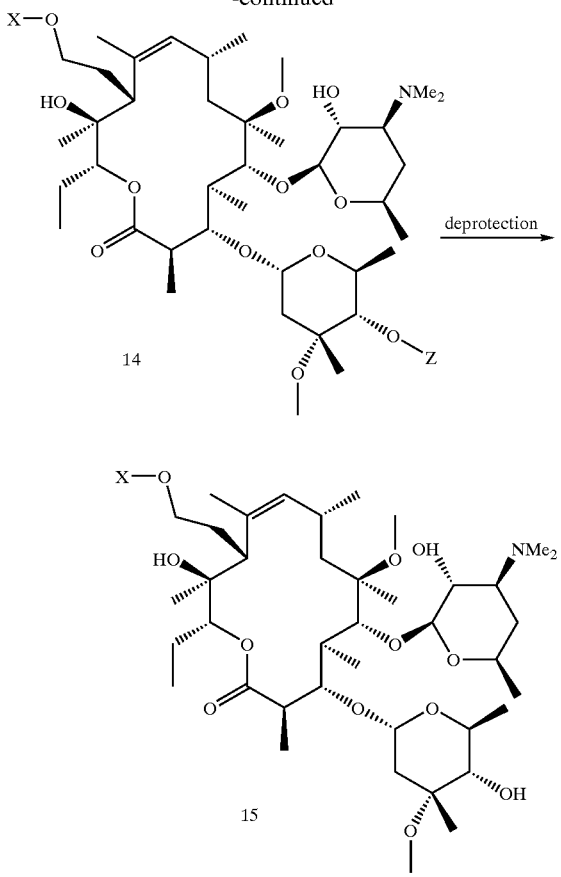

In another process of the present invention for the preparation of the compounds of formula I (as shown in Scheme 3), compound 6 from Scheme 1 is reduced with sodium cyanoborohydride, lithium borohydride, or the like, in a protic solvent such as methanol, ethanol, isopropanol or the like, or mixtures thereof, with an aprotic solvent such as THF, DME, or the like, at from about −20° C. to about 50° C., to provide compound 12. Compound 12 is then either alkylated or acylated to produce compound 13 where X is —$R_5$ or —C(O)$R_5$, and $R_5$ is as defined previously. The alkylating process is either performed with palladium catalyzed allylation with a tert-butyl allyl carbonate or is done with other alkylating agents, such as, for example, an alkyl halide, alkyl sulfonate, propargyl halide, allyl halide, benzylic halide, or the like, in the presence of a base such as sodium hydride, potassium hydride, potassium tert-butoxide, potassium hydroxide, KHMDS, or the like in an aprotic solvent such as THF, DMSO, DMF, dioxane, or the like, or mixtures thereof, at a temperature of from about −20° C. to about 60° C. The acylation process involves the use of a carboxylic acid, its anhydride or mixed anhydride, an acid halide or other activated acyl derivatives, optionally with the addition of a coupling agent such as DCC or the like, and optionally with the addition of DMAP and imidazole or the like. Compound 13 is treated with methanol as described in Scheme 1 to form compound 14. Compound 14 is then deprotected to provide compound 15 as described in Scheme 1.

Scheme 4

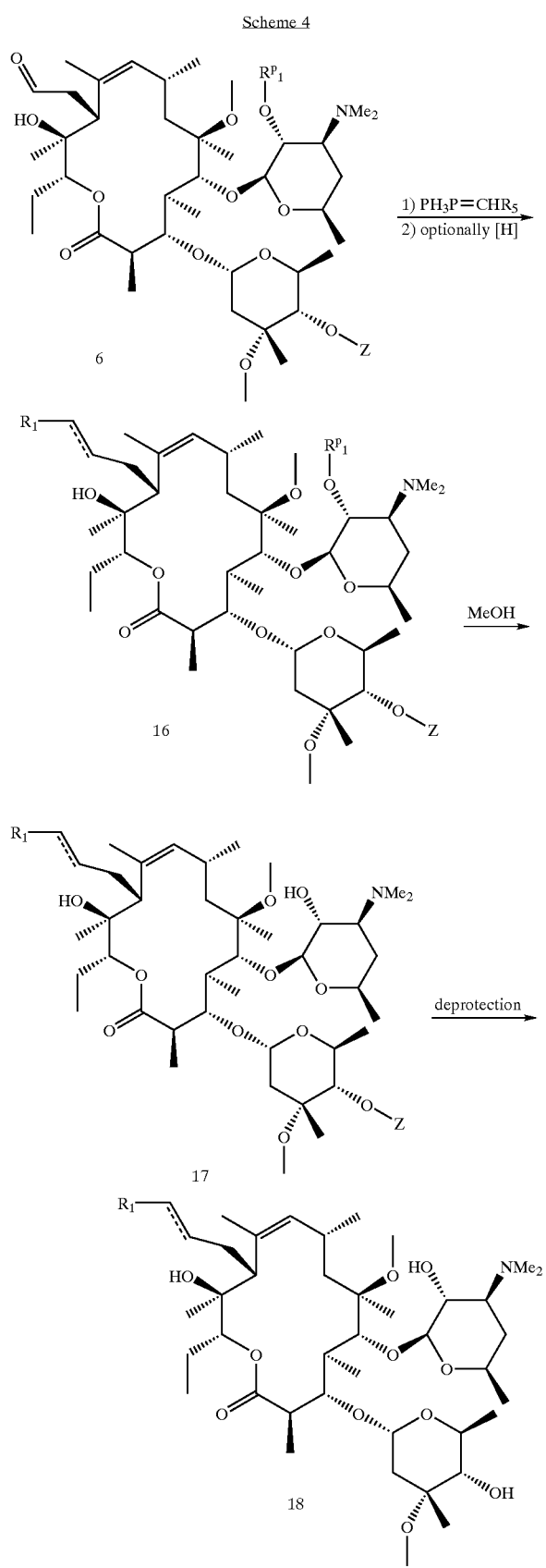

In another process of the present invention for the preparation of the compounds of formula I (as shown in Scheme 4), compound 6 from Scheme 1 is reacted with an alkyl, substituted alkyl, allylic, or propargylic phosphorane or phosphonate ylide in an aprotic solvent at a temperature of from about −20° C. to about 80° C. to afford compounds of formula 16, where $R_1$ is as defined previously. Compound 16 is optionally hydrogenated with palladium on carbon, platinum oxide, or the like under 1–4 atmospheres of hydrogen in an organic solvent such as methanol, ethanol, ethyl acetate or the like at a temperature of from about 0° C. to about 50° C. for 1–36 hours to provide the corresponding saturated linker at the C-11 position. Compound 16 is treated with methanol as described in Scheme 1 to form compound 17. Compound 17 is then deprotected to provide compound 18 as described in Scheme 1.

Scheme 5

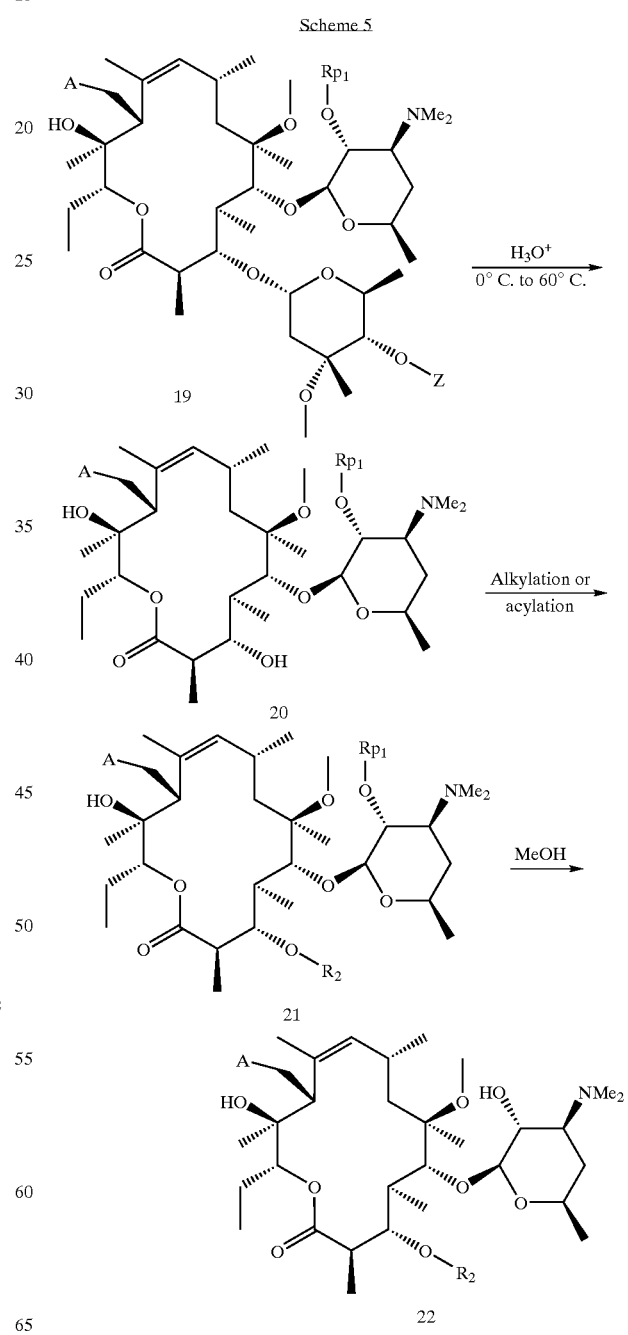

A process of the present invention for the preparation of the compounds of formula II (as shown in Scheme 5) includes the step of reacting compound 19 with dilute aqueous acid (0.1–2N) such as hydrochloric acid, sulfuric acid, trifluoroacetic acid, acetic acid or the like, optionally in a solvent such as water, acetone, acetonitrile, methanol, ethanol or the like, or combinations thereof, at a temperature of from about 0° C. to about 70° C. for 1–24 hours to provide compound 20. Compound 20 is then either alkylated or acylated to produce compound 21. The alkylating process is either done with palladium catalyzed allylation with tert-butyl allyl carbonate, as described in scheme 1, or is done with other alkylating agents, such as, for example, an alkyl halide, alkyl sulphonate, propargyl halide, allyl halide, benzylic halide, or the like, in the presence of a base such as sodium hydride, potassium hydride, potassium tert-butoxide, potassium hydroxide, KHMDS, or the like in an aprotic solvent such as THF, DMSO, DMF, dioxane, or the like, or mixtures thereof, at a temperature of from about −20° C. to about 60° C. The acylation process involves the use of a carboxylic acid, its anhydride or mixed anhydride, acid halide or other activated acyl derivatives, optionally with the addition of a coupling agent such as DCC or the like, and optionally with the addition of DMAP and imidazole or the like. Compound 21 can be treated with methanol as described in Scheme 1 to produce compound 22.

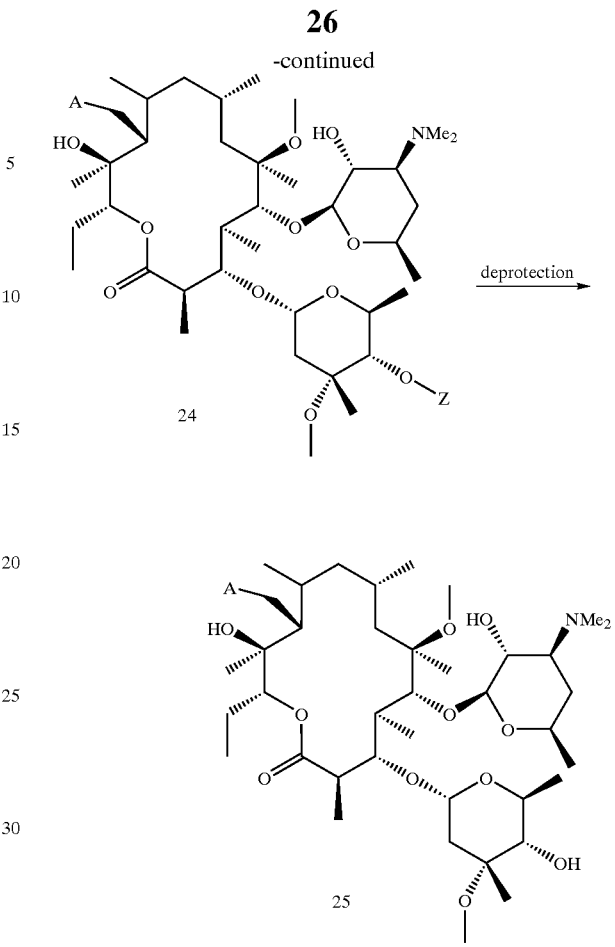

A process of the present invention for the preparation of the compounds of formula III (as shown in Scheme 6) includes the step of reacting compound 19 of Scheme 5 with palladium on carbon, platinum oxide, or the like under 1–50 atmospheres of hydrogen in an organic solvent such as methanol, ethanol, ethyl acetate or the like at a temperature of from about 0° C. to about 100° C. for 1–36 hours to provide the corresponding compound 23. Compound 23 is treated with methanol as described in Scheme 1 to form compound 24. Compound 24 is then deprotected as described in Scheme 1 to provide compound 25.

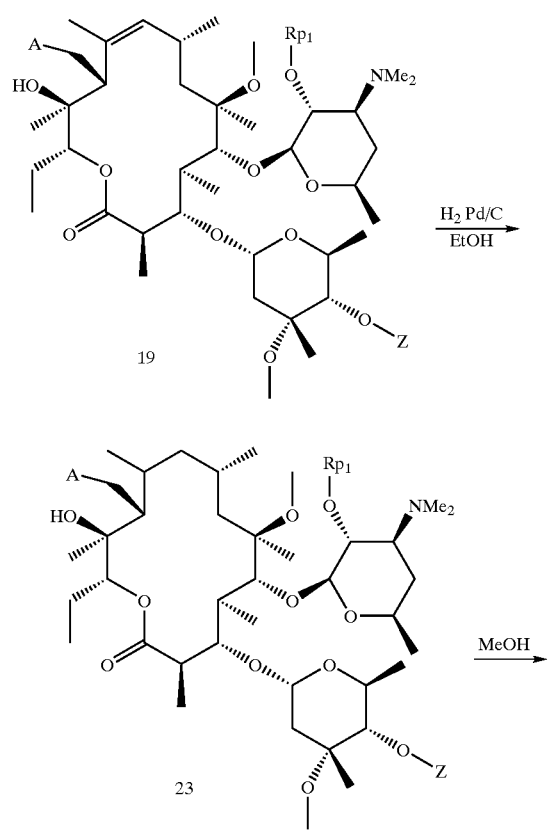

Scheme 6

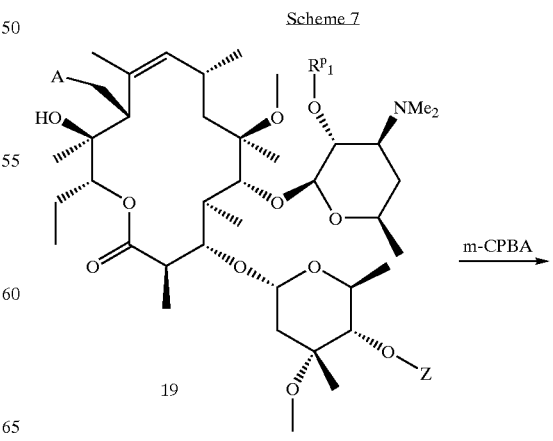

Scheme 7

27
-continued

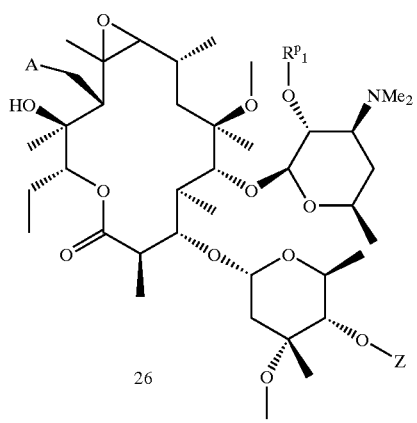

26

MeOH →

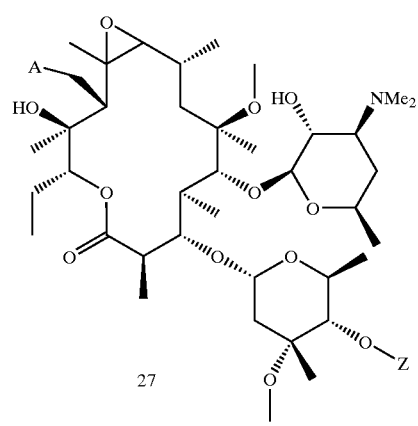

27

Deprotection →

28

Scheme 8

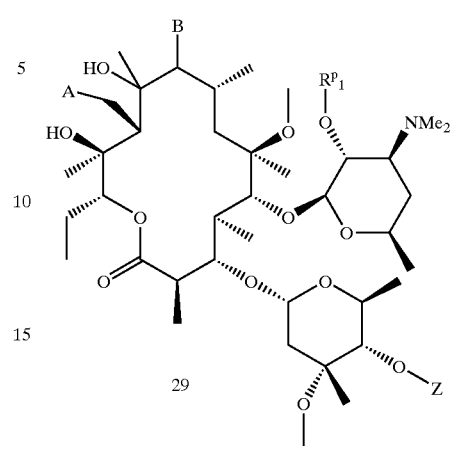

29

Nuc⁻ →

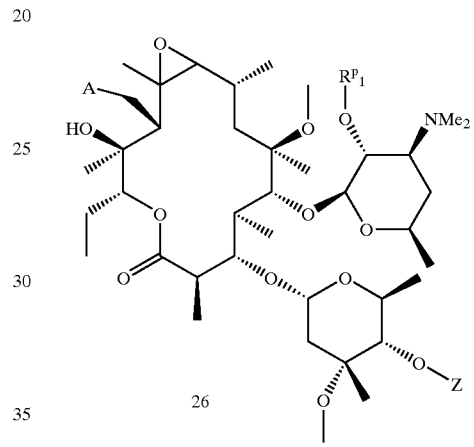

26

BF$_3$—Et$_2$O →

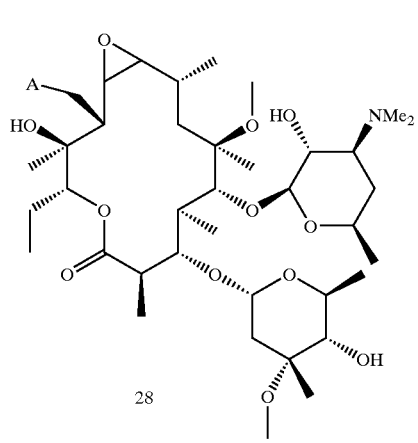

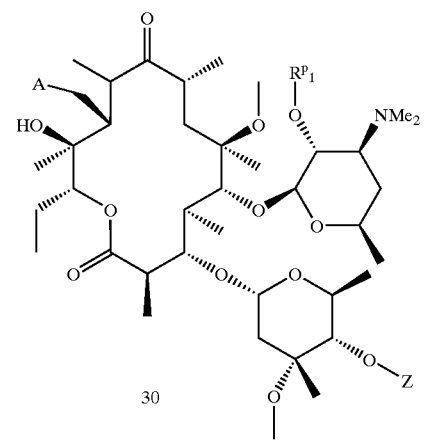

30

Another process of the present invention for the preparation of the compounds of formula III (as shown in Scheme 7) includes the step of reacting compound 19 of Scheme 5 with an oxidant such as m-CPBA, AcOOH, t-BuOOH or the like in an aprotic solvent to provide compound 26. Compound 26 is treated with methanol as described in Scheme 1 to form compound 27. Compound 27 is then deprotected as described in Scheme 1 to provide compound 28.

Another process of the present invention for the preparation of the compounds of formula III (as shown in Scheme 8) includes the step of alkylating compound 26 of Scheme 7 with an appropiate nucleophile, such as, for example, an alkyl, allylic, propargylic or aryl cuprate, or with azide, halide or cyanide anion, or the like, to afford compound 29 where B is an alkyl, allyl, or propargyl group, or a nitrile, halide or azide. Alternatively, compound 26 may be treated with a Lewis acid such as BF$_3$-etherate, MgBr$_2$-etherate, and the like, in an aprotic solvent to afford compound 30.

Scheme 9

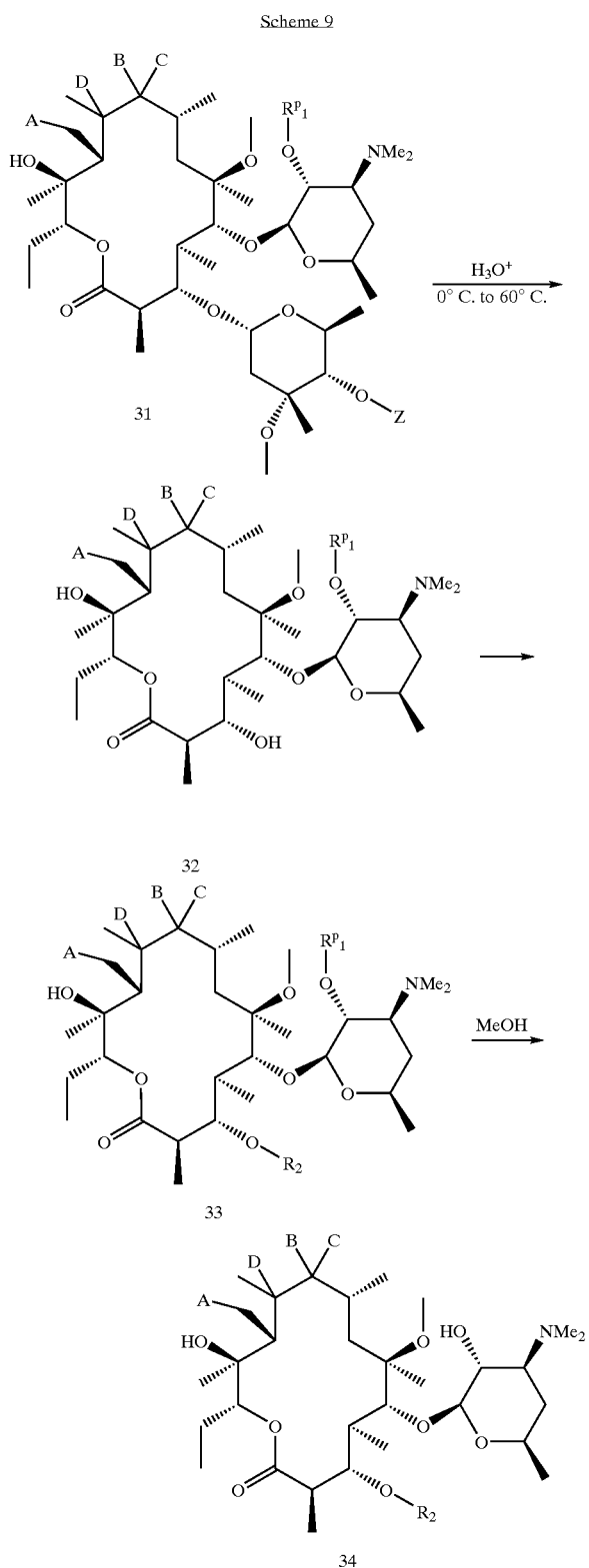

Another process of the present invention for the preparation of the compounds of formula IV (as shown in Scheme 9) includes the step of reacting compound 31 with dilute aqueous acid (0.1–2N) such as, for example, hydrochloric acid, sulfuric acid, trifluoroacetic acid, acetic acid or the like, optionally in a solvent such as water, acetone, acetonitrile, methanol, ethanol or the like, or combinations thereof, at a temperature of from about 0° C. to about 70° C. for 1–24 hours to provide compound 32. Compound 32 is then either alkylated or acylated to produce compound 33. The alkylating process is either done with palladium catalyzed allylation with tert-butyl allyl carbonate as described in scheme 1, or is done with other alkylating agents, such as, for example, an alkyl halide, alkyl sulphonate, propargyl halide, allyl halide, benzylic halide, or the like, in the presence of a base such as sodium hydride, potassium hydride, potassium tert-butoxide, potassium hydroxide, KHMDS, or the like in an aprotic solvent such as THF, DMSO, DMF, dioxane, or the like, or mixtures thereof, at a temperature of from about −20° C. to about 60° C. The acylation process involves the use of a carboxylic acid, its anhydride or mixed anhydride, acid halide or other activated acyl derivatives, optionally with the addition of a coupling agent such as DCC or the like, and optionally with the addition of DMAP and imidazole or the like. Compound 33 is treated with methanol as described in Scheme 1 to produce compound 34.

EXAMPLES

The procedures described above for preparing the compounds of the present invention will be better understood in connection with the following examples, which are intended to be illustrative only and not limiting of the scope of the invention. Various changes and modifications to the disclosed embodiments will be apparent to those skilled in the art. Such changes and modifications, including without limitation, those relating to the chemical structures, substituents, derivatives, intermediates, syntheses, formulations and/or methods of the invention may be made without departing from the spirit of the invention and the scope of the appended claims.

Example 1

Compound of Formula I: A=—CHO, $R_1$=H, Z=Ac and $Rp_1$=H

Step 1a. Compound 2 of Scheme (1): Z=Ac and $Rp_1$=Ac

Acetic anhydride (2.1 mL, 22 mmol) was added dropwise over 5 minutes to a stirred 0° C. solution of clarithromycin (7.48 g, 10 mmol), triethylamine (3.5 ml, 25 mmol), and DMAP (122 mg, 1 mmol) in 50 mL THF. The solution was stirred at 0° C. for 1 h, then allowed to warm to RT and stirred 14 hours. The reaction mixture was diluted with $CH_2Cl_2$ (200 mL) and washed with 10% aqueous $CuSO_4$ (2×200 mL) and with brine (1×100 mL). The aqueous washes were back-extracted with $CH_2Cl_2$ (3×200 mL) and the combined organic extracts dried on $K_2CO_3$, filtered, and concentrated in vacuo to give the title compound as a white solid (8.2 g). This material was subjected to silica gel chromatography (elution with 3% MeOH in $CH_2Cl_2$) to afford 8.1 g (97%) of analytically pure diacetate 2.

MS (ESI) m/z=832 (M+H)$^+$.

$^{13}$C NMR (100 MHz, $CDCl_3$): δ221.3, 175.7, 170.6, 100.1, 95.9, 80.3, 78.7, 78.4, 77.8, 76.7, 74.4, 72.9, 72.1, 69.3, 67.4, 63.3 (2), 50.7, 49.5, 45.4, 45.0, 40.9, 38.8, 38.7, 37.4, 35.3, 31.3, 21.7, 21.3 (2), 21.1, 19.9, 18.5, 18.1, 16.3, 16.1, 14.4, 12.5, 10.7, 9.2.

Step 1b. Compound 3 of Scheme 1: Z=Ac and $Rp_1$=Ac

A pressure tube was charged with the title compound of step 1a (832 mg, 1 mmol), triethylamine (0.42 mL, 3 mmol), and ethylene carbonate (5 g). The mixture was flushed with nitrogen, sealed, and heated in an oil bath maintained at 85–90° C. for 6 h. The mixture was then cooled, diluted with 50 mL $CH_2Cl_2$, and washed with $H_2O$ (100 mL) followed by brine (50 mL). The aqueous washes were back-extracted with $CH_2Cl_2$ (2×50 mL) and the combined organic extracts were dried ($K_2CO_3$), filtered, and concentrated in vacuo to give 3.9 g of a yellow solid. Purification by silica gel chromatography afforded the title compound (450 mg) along with 360 mg of unconverted starting material.

MS (ESI) m/z=815 (M+H)$^+$.

Step 1c. Compound 4 of Scheme 1: Z=Ac and $Rp_1$=Ac

Sodium borohydride (0.5 g, 13.3 mmol) was added portion-wise to a stirred methanolic solution of the compound from step 1b (3.6 g in 50 mL). This solution was allowed to warm to room temperature and stirred for 1 hour. The reaction mixture was diluted with 200 mL aqueous $NaHCO_3$ and extracted with ether (4×100 mL). The combined organic extracts were dried over $K_2CO_3$, filtered, and concentrated in vacuo to give 3.9 g of a solid residue which was purified by silica gel chromatography (elution with 2.5% MeOH/$CH_2Cl_2$, cont. $NH_3$) to afford 2.8 g (78%) of the title compound as a colorless solid.

MS (ESI) m/z=816 (M+H)$^+$.

Step 1d. Compound 5 of Scheme 1: Z=Ac and $Rp_1$=Ac

A 1 dram vial was charged with the compound of step 1c (100 mg, 0.12 mmol), butylvinyl ether (1 mL), and HgOAc (43 mg, 0.13 mmol). The vial was sealed and heated in a 60° C. oil bath for 2 h. The reaction mixture was cooled, diluted to 50 mL with ether, and washed with aqueous $NaHCO_3$ (2×25mL). The aqueous washes were back-extracted with ether (2×30 mL). The combined organic extracts were dried on $K_2CO_3$, filtered, and concentrated in vacuo to give 125 mg of a colorless oil which was purified by silica gel chromatography (elution with 2% MeOH in $CH_2Cl_2$ containing 0.2% $NH_3$) to afford the title compound as a colorless solid (94 mg, 93%).

MS (ESI) m/z=842 (M+H)$^+$.

Step 1e. Compound of Formula I: A=CHO, $R_1$=H, Z=Ac and $Rp_1$=Ac

A pressure tube equipped with a purge valve and thermowell was charged with the compound of step 1d (450 mg, 0.53 mmol), BHT (12 mg, 0.05 mmol), and toluene (150 mL). The mixture was degassed by alternately stirring under vacuum, and purging with dry nitrogen. The vessel was sealed and heated via electric heating tape secured to the outside of the tube and controlled with thermocouple regulation to maintain an internal temperature of 200° C. The reaction mixture was maintained at this temperature for 6 h then cooled and concentrated in vacuo to give 510 mg of yellow oil. The crude product was purified by silica gel chromatography (elution with 2.5% MeOH/$CH_2Cl_2$ cont. 0.2% $NH_3$) to afford 290 mg of the title compound, and 105 mg of unconverted starting material. The product is a mixture of two diastereomers at the hemiacetal in a ratio of 2:1.

MS (ESI) m/z=842 (M+H)$^+$.

$^{13}$C NMR (100 MHz, $CDCl_3$):δ176.5, 170.8, 170.2, 135.5, 129.9, 99.8, 95.36, 95.6, 86.6, 84.9, 83.2, 80.0, 79.7, 78.9, 76.1, 73.2, 72.5, 67.5, 63.3, 63.1, 56.8, 53.1, 51.6, 49.5, 45.7, 44.8, 43.0, 40.9, 40.0, 35.4, 31.6, 28.2, 23.9, 22.6, 21.8, 21.7, 21.5, 21.1, 18.7, 17.9, 15.7, 14.6, 10.8, 10.6.

Step 1f. Compound of Formula I: A=CHO, $R_1$=H, Z=Ac and $Rp_1$=H

The title compound of Step 1e (10 mg, 12 μmol) was taken up in 1 mL methanol and heated at 50° C. for 4 hours. The solution was concentrated in vacuo to afford 9 mg of the title compound as a colorless solid.

MS (ESI) m/z=800 (M+H)$^+$.

Example 2

Compound of Formula I: A=$CH_2OH$, $R_1$=H, Z=Ac and $Rp_1$=H

Step 2a. Compound of Formula I: A=$CH_2OH$, $R_1$=H, Z=Ac and $Rp_1$=Ac

The title compound from Example 1, Step 1e (50 mg, 59 μmol) was taken up in 2 mL absolute methanol and cooled to 0° C. Sodium borohydride (12 mg, 300 μmol) was added in one portion and the mixture was stirred at 0° C. for 30 min. then warmed to RT and stirred for an additional 1 h. The reaction mixture was diluted with 10 mL sat. aqueous $NaHCO_3$ and extracted with $CH_2Cl_2$ (4×10 mL) the combined organic extracts were dried on $K_2CO_3$, filtered, and concentrated to give 55 mg of a colorless solid. The crude product was purified by silica gel chromatography (elution with 3% MeOH in $CH_2Cl_2$ cont. 0.3% $NH_3$) to afford 42 mg of the title compound.

MS (ESI) m/z=844 (M+H)$^+$.

Step 2b. Compound of Formula I: A=$CH_2OH$, $R_1$=H, Z=Ac and $Rp_1$=H

The title compound of Step 2a (10 mg, 12 μmol) was taken up in 1 mL methanol and heated at 50° C. for 4 hours. The solution was concentrated in vacuo to afford 10 mg of the title compound as a colorless solid.

MS (ESI) m/z=802 (M+H)$^+$.

Example 3

Compound of Formula I: A=$CH_2OCO$-[3-quinolyl], $R_1$=H, Z=Ac and $Rp_1$=H

Step 3a. Compound of Formula I: A=$CH_2OCO$-[3-quinolyl], $R_1$=H, Z=Ac and $Rp_1$=Ac The title compound from Example 2 step 2a (5 mg, 7.2 μmol) was taken in 100 μL $CH_2Cl_2$. To this stirred solution was added sequentially 3-quinolinecarboxylic acid (1.2 mg, 7.2 μmol), DMAP (1.0 mg, 7.2 μmol), and DCC (36 μL of a 0.2M $CH_2Cl_2$ soln.). The mixture was stirred at RT for 1.5 h. then the entire solution was placed directly on a small silica gel column and eluted with 1.75% MeOH in $CH_2Cl_2$ to afford 5.3 mg of the title compound as a colorless solid (5.3 μmol 90%).

MS (ESI) m/z=999 (M+H)$^+$.

Step 3b. Compound of Formula I: A=$CH_2OCO$-[3-quinolyl], $R_1$=H, Z=Ac and $Rp_1$=H A methanolic solution of the compound of step 3a (3.5 mg in 0.25 mL) was heated at 50° C. for 18 h. The mixture was concentrated in vacuo and the crude product (3.5 mg) submitted to silica gel chromatography (elution with 2% MeOH in $CH_2Cl_2$ cont. 0.2% $NH_3$) to afford 1.8 mg of the title compound.

MS (ESI) m/z=957 (M+H)$^+$.

Example 4

Compound of Formula I: A=$CH_2OCO$-[4-quinolyl], $R_1$=H, Z=Ac and $Rp_1$=H

The title compound of Example 4 is prepared from the title compound of Step 2a and 4-quinolinecarboxylic acid according to the methods of Example 3.

Example 5

Compound of Formula I: A=CH=CH-phenyl, $R_1$=H, Z=Ac and $Rp_1$=H

Step 5a. Compound of Formula I: A=CH=CH-phenyl, $R_1$=H, Z=Ac and $Rp_1$=Ac

I) Formation of Ylide: To a stirred THF slurry of benzyltriphenylphosphonium bromide (216 mg, 0.5 mmol, in 1 mL THF) was added 0.5 mL NaHMDS (1M in THF) dropwise. The mixture was stirred at room temperature for 15 minutes and then cooled to −20° C.

II) Olefination: A THF solution of the title compound from Step 1e (200 mg, 240 μmol in 1 mL) was added dropwise to the above ylide solution. The mixture was stirred at −20° C. for 30 minutes, warmed to room temperature and stirred an additional 14 hours. The mixture was poured into sat. aq. NaHCO$_3$ (50 mL) and extracted with CH$_2$Cl$_2$ (3×25 mL). The combined organic extracts were dried (K$_2$CO$_3$), filtered, and concentrated to afford 430 mg of solid residue which was purified by silica gel chromatography to give the title compound as a mixture of E and Z isomers (158 mg, 170 μmol).

MS (ESI) m/z=916 (M+H)$^+$.

Step 5b. Compound of Formula I: A=CH=CH-phenyl. R$_1$=H, Z=Ac, and Rp$_1$=H

The title compound of Step 5a (100 mg, 109 μmol) was taken up in 5 mL methanol and heated at 50° C. for 4 hours. The solution was concentrated in vacuo to afford 89 mg of the title compound as a colorless solid.

MS (ESI) m/z=874 (M+H)$^+$.

Example 6

Compound of Formula I: A=CH$_2$NH-benzyl, R$_1$=H, Z=Ac and Rp$_1$=H.

Step 6a. Compound of Formula I: A=CH$_2$NH-benzyl, R$_1$=H, Z=Ac and Rp$_1$=Ac

To a methanol solution of the title compound of Step 1e of Example 1 (50 mg, 59 μmol in 0.5 mL) was added sequentially acetic acid (10 μL, 180 μmol), benzyl amine (7.8 μL 71), and sodium cyanoborohydride (8 mg, 120 μmol). The mixture was stirred at RT for 1 h. Mixture was quenched with 2 mL sat. aqueous NH$_4$Cl, and extracted with ether (3×2 mL). The aqueous layer was then raised to pH 10 by addition of 1N KOH and further extracted with CH$_2$Cl$_2$ (3×2 mL). The CH$_2$Cl$_2$ extracts were dried on K$_2$CO$_3$, filtered and concentrated to give 44 mg of residue which was purified by silica gel chromatography to give the title compound (30 mg) as a colorless solid.

MS (ESI) m/z=933 (M+H)$^+$.

Step 6b. Compound of Formula I: A =CH$_2$NH-benzyl , R$_1$=H, Z=Ac and Rp$_1$=H

The title compound from step 6a (5.0 mg) was dissolved in 0.5 mL methanol and stirred at 50° C. for 16 hours. The solution was concentrated in vacuo to give the title compound (4.8 mg) as a solid.

MS (ESI) m/z=945 (M+H)$^+$.

Example 7

Compound of Formula I: A=CH$_2$NH-allyl, R$_1$=H, Z=Ac and Rp$_1$=H

Step 7a. Compound of Formula I: A=CH$_2$NH-allyl, R$_1$=H, Z=Ac and Rp$_1$=Ac

To a methanol solution of the title compound from Example 1, Step 1e (40 mg, 48 μmol in 0.2 mL) was added sequentially acetic acid (10 μL, 180 μmol), allyl amine (4.4 μL 58 μmol), and sodium cyanoborohydride (6 mg, 96 μmol). The mixture was stirred at RT for 1 h. Mixture was quenched with 1 mL sat. aqueous NH$_4$Cl, and extracted with ether (3×2 mL). The aqueous layer was then raised to pH 10 by addition of 1N KOH and further extracted with CH$_2$Cl$_2$ (3×2 mL). The CH$_2$Cl$_2$ extracts were dried on K$_2$CO$_3$, filtered and concentrated to give 46 mg of residue which was purified by silica gel chromatography to give the title compound (27 mg) as an oil.

MS (ESI) m/z=883 (M+H)$^+$.

Step 7b. Compound of Formula I: A=CH$_2$NH-allyl, R$_1$=H, Z=Ac and Rp$_1$=H

The compound of Step 7a (10 mg) was treated according to the conditions described in Step 3b to afford 8 mg of the title compound.

Example 8

Compound of Formula II: A=CHO, R$_1$=H, R$_1$=H, and Rp$_1$=H

Step 8a. Compound of Formula II: A=CHO, R$_1$=H, R$_2$=H, and Rp$_1$=Ac

The title compound of Step 1e is taken up in 0.2 N aqueous hydrochloric acid and stirred at 50° C. for 2 hours. The solution is neutralized with saturated NaHCO$_3$ and extracted with CH$_2$Cl$_2$. The combined organic extracts are washed with brine, dried over K$_2$CO$_3$, filtered and concentrated to give the title compound.

Step 8b. Compound of Formula II: A=CHO, R$_1$=H, R$_2$=H, and Rp$_1$=H;

The product of Step 8a is treated according the procedure of Step 1f of Example 1 to afford the title compound.

Example 9

Compound of Formula II: A=CHO, R$_1$=H, R$_2$=benzoyl, and Rp$_1$=H

Step 9a. Compound of Formula II: A=CHO, R$_1$=H, R$_2$=benzoyl, and Rp$_1$=Ac

The title compound of step 8a is taken up in CH$_2$Cl$_2$ and stirred at −20° C. Triethylamine, DMAP, and benzoic anhydride are added sequentially to the stirred solution. The mixture is allowed to warm to room temperature and stirred for 6 hours. The reaction mixture is poured into saturated NaHCO$_3$ and extracted with CH$_2$Cl$_2$. The combined organic extracts are washed with brine, dried over K$_2$CO$_3$, filtered and concentrated to give the title product which is further purified by silica gel chromatography.

Step 9b. Compound of Formula II: A=CHO, R$_1$=H R$_2$=benzoyl, and Rp$_1$=H

The product of Step 9a is treated according the procedure of Step 1f of Example 1 to afford the title compound.

Example 10

Compound of Formula II: A=CH$_2$OH, R$_1$=H. R$_2$=H, and Rp$_1$=H

Step 10a. Compound of Formula II: A=CH$_2$OH, R$_1$=H, R$_2$=H, and Rp$_1$=Ac

The product of Step 2a of Example 2 is treated according to the procedure of Step 8a of Example 8 to provide the title compound.

Step 10b. Compound of Formula II: A=CH$_2$OH, R$_1$=H, R$_2$=H, and Rp$_1$=H

The product of Step 10a is treated according the procedure of Step 1f of Example 1 to afford the title compound.

Example 11

Compound of Formula II: A=CH$_2$OCO-[3-quinolyl], R$_1$=H, R$_2$=H and Rp$_1$=H

Step 11a. Compound of Formula I: A=CH$_2$OCO-[3-quinolyl], R$_1$=H, R$_2$=H and Rp$_1$=Ac The compound of Step 3a of Example 3 (22 mg) was taken up in 0.3 mL of 0.2N aqueous HCl. The solution was stirred at 50° C. for 2 hours. The reaction mixture was quenched with aqueous NaHCO$_3$ and extracted with CH$_2$Cl$_2$. The organic extracts were dried on K$_2$CO$_3$, filtered, and concentrated to afford 20 mg of residue. Purification of the crude product by silica gel chromatography gave 14 mg of the title compound as a white solid.

MS (ESI) m/z 799 (M+H)$^+$

Step 11b. Compound of Formula I: A=CH$_2$OCO-[3-quinolyl], R$_1$=H, R$_2$=H and Rp$_1$=H The title compound from step 11a (5.0 mg) was dissolved in 0.5 mL methanol and stirred at 50° C. for 12 hours. The solution was concentrated in vacuo to give the title compound (4.7 mg)
MS (ESI) m/z 747 (M+H)$^+$

Example 12
Compound of Formula II: A=CH$_2$OCO-[3-quinolyl], R$_1$=H, R$_2$=benzoyl and Rp$_1$=H
Step 12a. Compound of Formula II: A=CH$_2$OCO-[3-quinolyl], R$_1$=H, R$_2$=benzoyl and Rp$_1$=Ac
The product of Step 11a of Example 11 is treated according to the procedure of Step 9a of Example 9 to provide the title compound.
Step 12b. Compound of Formula II: A=CH$_2$OCO-[3-quinolyl], R$_1$=H, R$_2$=benzoyl and Rp$_1$=H
The product of Step 12a is treated according the procedure of Step 1f of Example 1 to afford the title compound.

Example 13
Compound of Formula II: A=CH$_2$OCO-[4-quinolyl], R$_1$=H, R$_2$=H, and Rp$_1$=H
Step 13a. Compound of Formula II: A=CH$_2$OCO-[4-quinolyl], R$_1$=H, R$_2$=H, and Rp$_1$=Ac
The product of Step 4a of Example 4 is treated according to the procedure of Step 8a of Example 8 to provide the title compound.
Step 13b. Compound of Formula II: A=CH$_2$OCO-[4-quinolyl], R$_1$=H, R$_2$=H and Rp$_1$=H
The product of Step 13a is treated according the procedure of Step 1f of Example 1 to afford the title compound.

Example 14
Compound of Formula II: A=CH$_2$=CH-phenyl, R$_1$=H, R$_2$=H, and Rp$_1$=H
Step 14a. Compound of Formula II: A=CH$_2$=CH-phenyl, R$_1$=H, R$_2$=H, and Rp$_1$=Ac
The product of Step 5a of Example 5 is treated according to the procedure of Step 8a of Example 8 to provide the title compound.
Step 14b. Compound of Formula II: A=CH$_2$=CH-phenyl, R$_1$=H R$_2$=H, and Rp$_1$=H
The product of Step 14a is treated according the procedure of Step 1f of Example 1 to afford the title compound.

Example 15
Compound of Formula II: A=CH$_2$NH-benzyl, R$_1$=H, R$_2$=H, and Rp$_1$=H
Step 15a. Compound of Formula II: A=CH$_2$NH-benzyl, R$_1$=H, R$_2$=H, and Rp$_1$=Ac
The product of Step 6a is treated according to the procedure of Step 8a of Example 8 to provide the title compound.
Step 15b. Compound of Formula II: A=CH$_2$NH-benzyl, R$_1$=H, R$_2$=H, and Rp$_1$=H
The product of Step 15a is treated according the procedure of Step 1f of Example 1 to afford the title compound.

Example 16
Compound of Formula II: A=CH$_2$NH-benzyl, R$_1$=H, R$_2$=benzoyl, and Rp$_1$=H
Step 16a. Compound of Formula II: A=CH$_2$NH-benzyl, R$_1$=H, R$_2$=benzoyl and Rp$_1$=Ac
The product of Step 15a of Example 15 is treated according to the procedure of Step 9a of Example 9 to provide the title compound.
Step 16b. Compound of Formula II: A=CH$_2$NH-benzyl, R$_1$=H, R$_2$=benzoyl, and Rp$_1$=H
The product of Step 16a is treated according to the procedure of Step 1f of Example 1 to provide the title compound.

Example 17
Compound of Formula II: A=CH$_2$NH-allyl, R$_1$=H, R$_2$=H, and Rp$_1$=H
Step 17a. Compound of Formula II: A=CH$_2$NH-allyl, R$_1$=H, R$_2$=H, and Rp$_1$=Ac
The product of Step 7a of Example 7 is treated according to the procedure of Step 8a of Example 8 to provide the title compound.
Step 17b. Compound of Formula II: A=CH$_2$NH-allyl, R$_1$=H, R$_2$=H, and Rp$_1$=H
The product of Step 17a is treated according the procedure of Step 1f of Example 1 to afford the title compound.

Example 18
Compound of Formula III: A=CHO, B=H, C=H, D=H, R$_1$=H, Z=Ac, and Rp$_1$=H
Step 18a. Compound of Formula III: A=CHO, B=H, C=H, D=H, R$_1$=H, Z=Ac and Rp$_1$=Ac
The title compound of Example 1, Step 1e is taken up in ethanol and stirred under hydrogen pressure (1 to 3 atm.) in the presence of palladium catalyst (10% Pd on C). The reaction mixture is filtered and concentrated in vacuo to afford the title compound.
Step 18b. Compound of Formula III: A=CHO, B=H, C=H, D=H, R$_1$=H, Z=Ac, and Rp$_1$=H
The title compound of Step 18a is treated according to the process of Step 1f of Example 1 to afford the title compound.

Example 19
Compound of Formula III: A=CHO, B and D taken together are —O—, C=H, R$_1$=H, Z=Ac, and Rp$_1$=H
Step 19a. Compound of Formula III: A=CHO, B and D taken together are —O—, C=H, R$_1$=H, Z=Ac, and Rp$_1$=Ac
The product of Step 1e of Example 1 and 10% molar excess of mCPBA are taken up in CH$_2$Cl$_2$ and stirred at room temperature for 2 hours. The reaction mixture is washed with dilute aqueous NaHSO$_3$ and the aqueous washes further extracted with CH$_2$Cl$_2$. The combined organic extracts are dried over K$_2$CO$_3$, filtered, and concentrated to give the crude product which is further purified by silica gel chromatography to afford the title compound.
Step 19b. Compound of Formula III: A=CHO, B and D taken together are —O—, C=H, R$_1$=H, Z=Ac, and Rp$_1$=H
The product of Step 19a is treated according the procedure of Step 1f of Example 1 to afford the title compound.

Example 20
Compound of Formula III: A=CHO, B and C taken together are =O, D=H, R$_1$=H Z=Ac, and Rp$_1$=H
Step 20a. Compound of Formula III: A=CHO, B and C taken together are =O, D=H, R$_1$=H, Z=Ac, and Rp$_1$=Ac
The product of Step 19a of Example 19 is taken up in anhydrous ether and stirred at −78° C. while a 1.5-fold molar excess of BF$_3$·Et$_2$O is added dropwise. The solution is allowed to warm slowly to room temperature and stirred at this temperature for 4 hours. The reaction mixture is partitioned between sat. aq. NaHCO$_3$ and ether. The aqueous layer is separated and further extracted with CH$_2$Cl$_2$. The combined organic extracts are dried on MgSO$_4$, filtered and concentrated to give the title compound.
Step 20b. Compound of Formula III: A=CHO, B and C taken together are =O, D=H, R$_1$=H, Z=Ac, and Rp$_1$=H
The product of Step 20a is treated according the procedure of Step 1f of Example 1 to afford the title compound.

Example 21
Compound of Formula III: A=CHO, B=OH, D=OH, C=H, $R_1$=H, Z=H, and $Rp_1$=H The product of Step 1f of Example 1 and an equimolar quantity of NMO are taken up in t-BuOH and stirred at room temperature. A catalytic quantity of $OsO_4$ (4% solution in $H_2O$) is then added dropwise and the mixture stirred at room temperature for 16 hours. The reaction mixture is diluted with water and extracted with $CH_2Cl_2$. The combined organic extracts are washed with brine, dried over $K_2CO_3$, filtered, and concentrated in vacuo to give the crude title product which is further purified by silica gel chromatography.

Example 22
Compound of Formula III: A=$CH_2OH$, B=H, C=H, D=H, $R_1$=H, Z=Ac, and $Rp_1$=H Step 22a. Compound of Formula III: A=$CH_2$ OH, B=H, C=H, D=H, $R_1$=H, Z=Ac, and $Rp_1$=Ac The title compound of Example 2, Step 2a is taken up in ethanol and stirred under hydrogen pressure (1 to 3 atm.) in the presence of palladium catalyst (10% Pd on C). The reaction mixture is filtered and concentrated in vacuo to afford the title compound.

Step 22b. Compound of Formula III: $CH_2OH$, B=H, C=H, D=H, $R_1$=H, Z=Ac, and $Rp_1$=H The title compound of Step 22a is treated according to the process of Step 1f of Example 1 to afford the title compound.

Example 23
Compound of Formula III: A=$CH_2OH$, B and D taken together are —O—, C=H, D=H, $R_1$=, Z=Ac, and $Rp_1$=H Step 23a. Compound of Formula III: A=$CH_2OH$, B and C taken together are —O—, D=H, $R_1$=H, Z=Ac, and $Rp_1$=Ac The product of Step 2a of Example 2 is treated according to the procedure of Step 19a of Example 19 to afford the title compound.

Step 23b. Compound of Formula III: A=$CH_2OH$, B and C taken together are —O—, D=H, $R_1$=H, Z=Ac, and $Rp_1$=H;

The product of Step 23a is treated according to the procedure of Step 1f of Example 1 to afford the title compound.

Example 24
Compound of Formula III: A=$CH_2OH$, B and C taken together are =O, D=H, $R_1$=H, Z=Ac, and $Rp_1$=H Step 24a. Compound of Formula III: A=$CH_2OH$, B and C taken together are =O, D=H, $R_1$=H, Z=Ac, and $Rp_1$=Ac The product of Step 23a of Example 23 is treated according to the procedure of Step 20a of Example 20 to afford the title compound.

Step 24b. Compound of Formula III: A=$CH_2OH$, B and C taken together are =O, D=H, $R_1$=H, Z=Ac, and $Rp_1$=H The product of Step 24a is treated according to the procedure of Step 1f of Example 1 to afford the title compound.

Example 25
Compound of Formula III: A=$CH_2OH$, B=OH, D=OH, C=H, $R_1$=H, Z=Ac, and $Rp_1$=H The product of Step 2b of Example 2 is treated according to the procedure of Step 21a of example 21 to provide the title compound.

Example 26
Compound of Formula III: A=$CH_2OCO$-[3-quinolyl], B=H, C=H, D=H, $R_1$=H, Z=Ac and $Rp_1$=H Step 26a. Compound of Formula I: A=$CH_2OCO$-[3-quinolyl], B=H, C=H, D=H, $R_1$=H, Z=Ac and $Rp_1$=Ac The title compound of Step 22a is processed according the procedures of Step 3a to afford the title compound.

Step 26b. Compound of Formula I: A=$CH_2OCO$-[3-quinolyl], B=H, C=H, D=H, $R_1$=H, Z=Ac and $Rp_1$=H The compound of Step 26a is treated according to the process of Step 3b to afford the title compound.

Example 27
Compound of Formula III: A=$CH_2OCO$-[3-quinolyl], B and D taken together are —O—, C=H, $R_1$=H, Z=Ac, and $Rp_1$=H Step 27a. Compound of Formula III: A=$CH_2OCO$-[3-quinolyl], B and D taken together are —O—, C=H, $R_1$=H, Z=Ac, and $Rp_1$=Ac The product of Step 3a of Example 3 is treated according to the procedure of Step 19a of Example 19 to afford the title compound.

Step 27b. A=$CH_2OCO$-[3-quinolyl], B and D taken together are —O—, C=H, $R_1$=H, Z=Ac, and $Rp_1$=H The product of Step 27a is treated according to the procedure of Step 1f of Example 1 to afford the title compound.

Example 28
Compound of Formula III: A=$CH_2OCO$-[3-quinolyl], B and C taken together are =O, D=H, $R_1$=H, Z=Ac, and $Rp_1$=H The title compound is prepared according to the procedures of Example 20 using the product of Step 27b of Example 27 as the starting material.

Example 29
Compound of Formula III: A=$CH_2OCO$-[3-quinolyl], B=OH, D=OH, C=H, $R_1$=H, Z=Ac and $Rp_1$=H The title compound is synthesized according to the procedures of Example 21 using the product of Step 3b of Example 3 as the starting material.

Example 30
Compound of Formula III: A=$CH_2OCO$-[4-quinolyl], B=H, C=H, D=H, $R_1$=H, Z=Ac, and $Rp_1$=H The product of Step 4b of Example 4 is treated according to the procedure of Step 18a of Example 18 to afford the title compound.

Example 31
Compound of Formula III: A=$CH_2OCO$-[4-quinolyl], B and D taken together are —O—, C=H, $R_1$=H, Z=Ac, and $Rp_1$=H The title compound is formed according to the procedures of Example 19 using the compound of Step 4a of Example 4 as the starting material.

Example 32
Compound of Formula III: A=$CH_2OCO$-[4-quinolyl], B and C taken together are =O, D=H, $R_1$=H, Z=Ac, and $Rp_1$=H The title compound is formed according to the procedures of Example 20 using the title compound of Example 31 as the starting material.

Example 33

Compound of Formula III: A=CH$_2$OCO-[4-quinolyl], B=OH, D=OH, C=H, R$_1$=H, Z=Ac, and Rp$_1$=H The title compound is synthesized according to the procedures of Example 21 using the product of Step 4b of Example 4 as the starting material.

Example 34

Compound of Formula III: A=CH=CH-phenyl, B=H, C=H, D=H, R$_1$=H, Z=Ac, and Rp$_1$=H Step 34a. Compound of Formula III: A=CH=CH-phenyl, B=H, C=H, D=H, R$_1$=H, Z=Ac, and Rp$_1$=Ac The product of Step 18a of Example 18 is treated according to the procedure of Step 5a of Example 5 to afford the title compound.

Step 34b. Compound of Formula III: A=CH=CH-phenyl, B=H, C=H, D=H, R$_1$=H, Z=Ac, and Rp$_1$=H The product of Step 34a is treated according to the procedure of Step 1f of Example a to afford the title compound.

Example 35

Compound of Formula III: A=CH$_2$NH-benzyl, B=H, C=H, D=H, R$_1$=H, Z=Ac, and Rp$_1$=H Step 35. Compound of Formula III: A=CH$_2$NH-benzoyl, B=H, C=H, D=H, R$_1$=H, Z=Ac, and Rp$_1$=H The product of step 18b is treated according to the procedure of step 6a to afford the title compound.

Example 36

Compound of Formula III: A=CH$_2$NH-benzyl, B and D taken together are —O—, C=H, R$_1$=H, Z=Ac, and Rp$_1$=H Step 36a. Compound of Formula III: A=CH$_2$NH-benzyl, B and D taken together are —O—, C=H, R$_1$=H, Z=Ac, and Rp$_1$=Ac The title compound is prepared according to the procedures of step 21a of Example 21 using compound 6a of Example 6 as the starting material.

Step 36b. Compound of Formula III: A=CH$_2$NH-benzyl, B and D taken together are —O—, C=H, R$_1$=H, Z=Ac, and Rp$_1$=H The product of Step 36a is treated according to the procedure of Step 1f of Example a to afford the title compound.

Example 37

Compound of Formula III: A=CH$_2$NH-benzyl, B and C taken together are =O, D=H, R$_1$=H, Z=Ac, and Rp$_1$=H The title compound is formed according to the procedures of Example 20 using the title compound of Step 36a as the starting material.

Example 38

Compound of Formula III: A=CH$_2$NH-benzyl, B=OH, D=OH, C=H, R$_1$=H, Z=Ac and Rp$_1$=H The title compound is synthesized according to the procedures of Example 21 using the product of Step 6b of Example 6 as the starting material.

Example 39

Compound of Formula III: A=CH$_2$NH-allyl, B=H, C=H, D=H, R$_1$=H, Z=Ac, and Rp$_1$=H Step 39a. Compound of Formula III: A=CH$_2$NH-allyl, B=H, C=H, D=H, R$_1$=H, Z=Ac, and Rp$_1$=Ac The product of Step 18a of Example 18 is treated according to the procedure of Step 7a of Example 7 to afford the title compound.

Step 39b. Compound of Formula III: A=CH$_2$NH-allyl, B=H, C=H, D=H, R$_1$=H, Z=H, and Rp$_1$=H The product of Step 39a is treated according to the procedure of Step 1f of Example 1 to afford the title compound.

Example 40

Compound of Formula III: A=CH$_2$NH-allyl, B and D taken together are —O—, C=H, R$_1$=H, Z=Ac, and Rp$_1$=H The title compound is formed according to the processes of Example 19 using product of Step 7a of Example 7 as the starting material.

Example 41

Compound of Formula III:: A=CH$_2$NH-allyl, B and C taken together are =O, D=H, R$_1$=H, Z=Ac, and Rp$_1$=H The title compound is formed according to the procedures of Example 20 using the title compound of Example 40 as the starting material.

Example 42

Compound of Formula III: A=CH$_2$NH-allyl, B=OH, D=OH, C=H, R$_1$=H, Z=Ac, and Rp$_1$=H The title compound is synthesized according to the procedures of Example 21 using the product of Step 7b of Example 7 as the starting material.

Example 43

Compound of Formula IV: A=CHO, B=H, C=H, D=H, R$_1$=H, R$_2$=H, and Rp$_1$=H

The product of Step 18a is treated according to the processes of Example 8 to afford the title compound.

Example 44

Compound of Formula IV: A=CHO, B and D taken together are —O—, C=H, R$_1$=H, R$_2$=H, and Rp$_1$=H The product of Step 19a is treated according to the processes of Example 8 to afford the title compound.

Example 45

Compound of Formula IV: A=CHO, B and C taken together are =O, D=H, R$_1$=H, R$_2$=H, and Rp$_1$=H The product of step 20a is treated according to the processes of Example 8 to afford the title compound.

Example 46

Compound of Formula IV: A=CHO, B=OH, D=OH, C=H, R$_1$=H, R$_2$=H, and Rp$_1$=H

The product of Step 21a of Example 21 is treated according to the processes of Example 8 to afford the title compound.

Example 47

Compound of Formula IV: A=CH$_2$OH, B=H, C=H, D=H, R$_1$=H, R$_2$=H, and Rp$_1$=H The product of Step 22a is treated according to the processes of Example 8 to afford the title compound.

Example 48

Compound of Formula IV: A=CH$_2$OH, B and D taken together are —O—, C=H, R$_1$=H, R$_2$=H, and Rp$_1$=H The product of Step 23a is treated according to the processes of Example 8 to afford the title compound.

Example 49

Compound of Formula IV: A=CH$_2$OH, B and C taken together are =O, D=H, R$_1$=H R$_2$=H, and Rp$_1$=H The product of Step 24a of Example 24 is treated according to the processes of Example 8 to afford the title compound.

Example 50

Compound of Formula IV: A=CH$_2$OH, B=OH, D=OH, C=H, R$_1$=H, R$_2$=H, and Rp$_1$=H The product of step 25 is treated according to the processes of Example 8 to afford the title compound.

Example 51

Compound of Formula IV A=CH$_2$OCO-[3-quinolyl], B=H, C=H, D=H, R$_1$=H, R$_2$=H, and Rp$_1$=H The product of Step 26a of Example 26 is treated according to the processes of Example 8 to afford the title compound.

Example 52

Compound of Formula IV: A=CH$_2$OCO-[3-quinolyl], B and D taken together are —O—, C=H, R$_1$=H, R$_2$=H, and Rp$_1$=H The product of Step 27a of Example 27 is treated according to the processes of Example 8 to afford the title compound.

Example 53

Compound of Formula IV: A=CH$_2$OCO-[3-quinolyl], B and C taken together are =O, D=H, R$_1$=H, R$_2$=H, and Rp$_1$=H The product of Example 28 is treated according to the processes of Example 8 to afford the title compound.

Example 54

Compound of Formula IV: A=CH$_2$OCO-[3-quinolyl], B=OH, D=OH, C=H, R$_1$=H R$_2$=H, and Rp$_1$=H The product of Example 29 is treated according to the processes of Example 8 to afford the title compound.

Example 55

Compound of Formula IV: A=CH$_2$OCO-[4-quinolyl], B=H, C=H, D=H, R$_1$=H, R$_2$=H, and Rp$_1$=H The product of Example 30 is treated according to the processes of Example 8 to afford the title compound.

Example 56

Compound of Formula IV: A=CH$_2$OCO-[4-quinolyl], B and D taken together are —O—, C=H, R$_1$=H, R$_2$=H, and Rp$_1$=H The product of Example 31 is treated according to the processes of Example 8 to afford the title compound.

Example 57

Compound of Formula IV: A=CH$_2$OCO-[4-quinolyl], B and C taken together are =O, D=H, R$_1$=H, R$_2$=H, and Rp$_1$=H The product of Example 32 is treated according to the processes of Example 8 to afford the title compound.

Example 58

Compound of Formula IV: A=CH$_2$OCO-[4-quinolyl], B=OH, D=OH, C=H, R$_1$=H, R$_2$=H, and Rp$_1$=H The product of Example 33 is treated according to the processes of Example 8 to afford the title compound.

Example 59

Compound of Formula IV: A=CH=CH-phenyl, B=H, C=H, D=H, R$_1$=H, R$_2$=H, and Rp$_1$=H The product of Step 34a of Example 34 is treated according to the processes of Example 8 to afford the title compound.

Example 60

Compound of Formula IV: A=CH$_2$NH-benzyl, B=H, C=H, D=H, R$_1$=H, R$_2$=H, and Rp$_1$=H The product of Example 35 is treated according to the processes of Example 8 to afford the title compound.

Example 61

Compound of Formula IV: A=CH$_2$NH-benzyl, B and D taken together are —O—, C=H, R$_1$=H, R$_2$=H, and Rp$_1$=H The product of Step 36a of Example 36 is treated according to the processes of Example 8 to afford the title compound.

Example 62

Compound of Formula IV: A=CH$_2$NH-benzyl, B and C taken together are =O, D=H, R$_1$=H, R$_2$=H, and Rp$_1$=H The product of Example 37 is treated according to the processes of Example 8 to afford the title compound.

Example 63

Compound of Formula IV: A=CH$_2$NH-benzyl, B=OH, D=OH, C=H, R$_1$=H, R$_2$=H, and Rp$_1$=H The product of Example 38 is treated according to the processes of Example 8 to afford the title compound.

Example 64

Compound of Formula IV: A=CH$_2$NH-allyl, B=H, C=H, D=H, R$_1$=H, R$_2$=H, and Rp$_1$=H The product of Step 39a of Example 39 is treated according to the processes of Example 8 to afford the title compound.

Example 65

Compound of Formula IV: A=CH$_2$NH-allyl, B and D taken together are —O—, C=H, R$_1$=H, R$_2$=H, and Rp$_1$=H The product of Example 40 is treated according to the processes of Example 8 to afford the title compound.

Example 66

Compound of Formula IV: A=CH$_2$NH-allyl, B and C taken together are =O, D=H, R$_1$=H, R$_2$=H, and Rp$_1$=H The product of Example 41 is treated according to the processes of Example 8 to afford the title compound.

Example 67

Compound of Formula IV: A=CH$_2$NH-allyl, B=OH, D=OH, C=H, R$_1$=H, R$_2$=H, and Rp$_1$=H The product of Example 42 is treated according to the processes of Example 8 to afford the title compound.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by formula

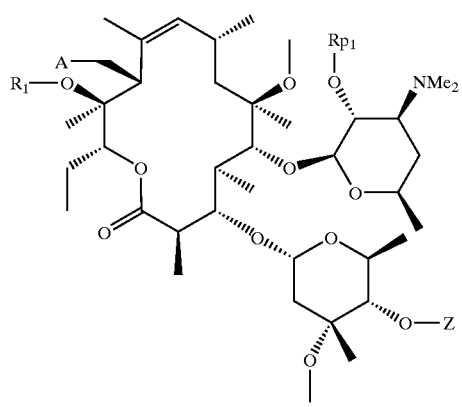

(I)

or

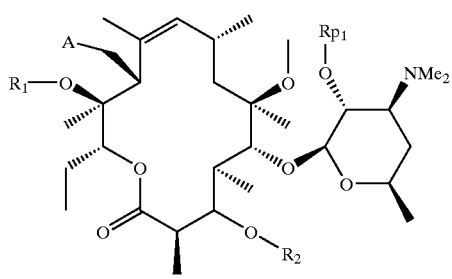

(II)

or

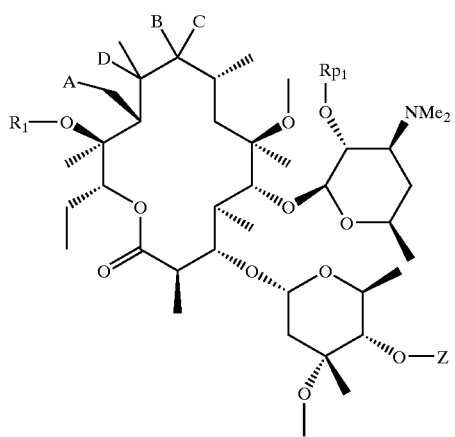

(III)

or

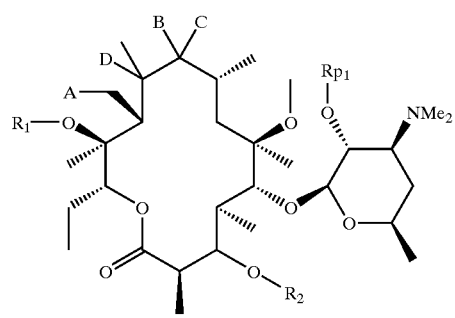

(IV)

or a pharmaceutically acceptable ester, salt or prodrug thereof,
wherein
A is selected from the group consisting of
(1) $C_1$–$C_6$-alkyl, $C_2$–$C_6$-alkenyl or $C_2$–$C_6$-alkynyl, optionally substituted with one or more substituents selected from the group consisting of:

i. halogen;
ii. aryl;
iii. substituted aryl;
iv. heterocyclic;
v. substituted heterocyclic;
vi. —O—$R_5$, where $R_5$ is selected from the group consisting of:
  1. hydrogen;
  2. aryl;
  3. substituted aryl;
  4. heterocyclic; and
  5. substituted heterocyclic;
vii. —O—$C_1$–$C_6$-alkyl-$R_5$, where $R_5$ is as previously defined;
viii. —O—$C_2$–$C_6$-alkenyl-$R_5$, where $R_5$ is as previously defined;
ix. —O—$C_2$–$C_6$-alkynyl-$R_5$, where $R_5$ is as previously defined; and
x. —$NR_6R_7$, where $R_6$ and $R_7$ are each independently selected from the group consisting of:
  a. hydrogen;
  b. $C_1$–$C_6$-alkyl, optionally substituted with one or more substituents selected from the group consisting of:
    (I) halogen;
    (II) aryl;
    (III) substituted aryl;
    (IV) heterocyclic; and
    (V) substituted heterocyclic;
  c. $C_2$–$C_6$-alkenyl, optionally substituted with one or more substituents selected from the group consisting of:
    (I) halogen;
    (II) aryl;
    (III) substituted aryl;
    (IV) heterocyclic; and
    (V) substituted heterocyclic; and
  d. $C_2$–$C_6$-alkynyl, optionally substituted with one or more substituents selected from the group consisting of:
    (I) halogen;
    (II) aryl;
    (III) substituted aryl;
    (IV) heterocyclic; and
    (V) substituted heterocyclic; or
  e. $R_6$ $R_7$ taken with the nitrogen atom to which they are connected form a 3- to 7-membered ring which may optionally contain one or more functions selected from the group consisting of:
    (I) —O—;
    (II) —NH—;
    (III) —N($C_1$–$C_6$-alkyl)-;
    (IV) —N(aryl)-;
    (V) —N(heteroaryl)-;
    (VI) —S—;
    (VII) —S(O)—; and
    (VIII) —S(O)$_2$—
    (IX) —C(O)—,
(2) —C(O)—$R_5$, where $R_5$ is as previously defined;
(3) —C(O)—$C_1$–$C_6$-alkyl-$R_5$, where $R_5$ is as previously defined;
(4) —C(O)—$C_2$–$C_6$-alkenyl-$R_5$, where $R_5$ is as previously defined;
(5) —C(O)—$C_2$–$C_6$-alkynyl-$R_5$, where $R_5$ is as previously defined;
(6) $C_1$–$C_6$-alkyl-M-$R_5$, where M is —OC(O)—, —OC(O)O—, —OC(O)$NR_6$—, —C(O)$NR_6$—, —$NR_6$C(O)—, —NR$_6$C(O)O—, —NR$_6$C(O)NR$_7$—, —NR$_6$C(NH)NR$_7$— or S(O)$_n$—, where n=0, 1 or 2, and where R$_5$, R$_6$, R$_7$ are as previously defined;
(7) —C$_2$–C$_6$-alkenyl-M—R$_5$, where M and R$_5$ are as previously defined; and
(8) —C$_2$–C$_6$-alkynyl-M—R$_5$, where M and R$_5$ are as previously defined;

B, C, and D may be present singly or in combination and are independently selected from the group consisting of:
(1) hydrogen;
(2) halogen;
(3) C$_1$–C$_6$-alkyl;
(4) aryl;
(5) substituted aryl;
(6) heteroaryl;
(7) substituted heteroaryl;
(11) B and C taken together are =N—N—R$_6$R$_7$, where R$_6$ and R$_7$ are as previously defined;
(12) B and D taken together are —O—;
(13) B and D taken together are —S—;
(14) B and D taken together are —N(R$_6$)—, where R$_6$ is as previously defined; and
(15) B and D taken together with the carbon atoms to which they are attached form a 4- to 8-membered ring which may optionally contain one or more functions selected from the group consisting of:
　i. —O—;
　ii. —NH—;
　iii. —N(C$_1$–C$_6$-alkyl)-;
　iv. —N(aryl)-;
　v. —N(heteroaryl)-;
　vi. —S—;
　vii. —S(O)—;
　viii. —S(O)$_2$—; and
　ix. —C(O)—;

R$_1$ is selected from the group consisting of:
(1) hydrogen;
(2) R$_3$, where R$_3$ is C$_1$–C$_6$-alkyl, C$_2$–C$_6$-alkenyl or C$_2$–C$_6$-alkynyl, optionally substituted with one or more substituents selected from the group consisting of:
　i. halogen;
　ii. aryl;
　iii. substituted-aryl;
　iv. heteroaryl;
　v. substituted-heteroaryl;
　vi. —O—C$_1$–C$_6$-alkyl-R$_5$, where R$_5$ is as previously defined; and
　vii. —N—R$_6$R$_7$, where R$_6$ and R$_7$ are as previously defined;
(3) —C(O)—R$_4$, where R$_4$ is hydrogen or R$_3$, where R$_3$ is as previously defined;
(4) —C(O)O—R$_3$, where R$_3$ is as previously defined; and
(5) —C(O)N—R$_6$R$_7$, where R$_6$ and R$_7$ are as previously defined;

R$_2$ is selected from the group consisting of:
(1) a hydroxy protecting group;
(2) R$_5$, where R$_5$ is as previously defined;
(3) —X—Y—R$_5$, where X is —C(O), —C(O)O—, —C(O)NR$_6$—, or absent, and Y is C$_1$–C$_6$-alkyl or absent, where R$_5$ and R$_6$ are as previously defined; and
(4) C$_1$–C$_6$-alkyl, C$_2$–C$_6$-alkenyl or C$_2$–C$_6$-alkynyl optionally substituted with one or more substituents selected from the group consisting of:
　i. halogen;
　ii. aryl;
　iii. substituted-aryl;
　iv. heteroaryl;
　v. substituted-heteroaryl;
　vi. —O—R$_5$ where R$_5$, is as previously defined;
　vii. —O—C$_1$–C$_6$-alkyl-R$_5$, where R$_5$ is as previously defined;
　viii. —O—C$_2$–C$_6$-alkenyl-R$_5$, where R$_5$ is as previously defined;
　ix. —O—C$_2$–C$_6$-alkynyl-R$_5$, where R$_5$ is as previously defined; and
　x. —N—R$_6$R$_7$, where R$_6$ and R$_7$ are as previously defined;

Rp$_1$ is hydrogen or a hydroxy protecting group; and

Z is selected from the group consisting of:
(1) hydrogen;
(2) a hydroxy protecting group; and
(3) —X—R$_3$, where X and R$_3$ are as previously defined.

2. A compound according to claim 1 which is represented by the formula:

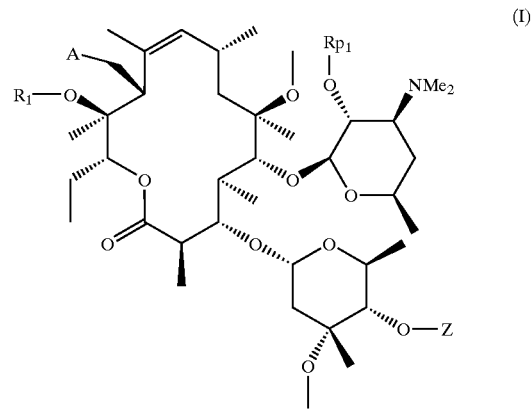

(I)

3. A compound according to claim 2 wherein R$_1$ and Z are hydrogen.

4. A compound according to claim 1 which is represented by formula:

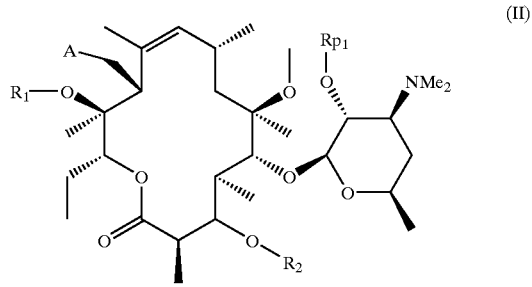

(II)

5. A compound according to claim 4 wherein R$_1$ is hydrogen.

6. A compound according to claim 1 which is represented by the formula:

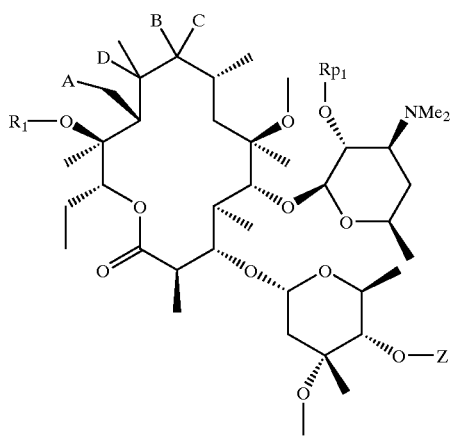

(III)

7. A compound according to claim 6 wherein $R_1$ and Z are hydrogen.

8. A compound according to claim 1 which is represented by the formula:

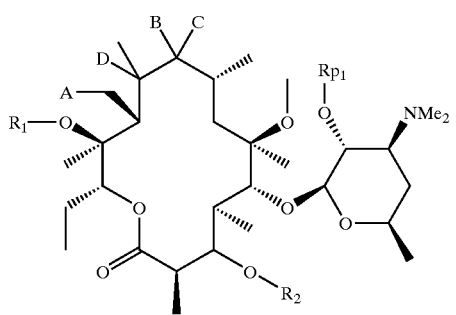

(IV)

9. A compound according to claim 8 wherein $R_1$ is hydrogen.

10. A pharmaceutical composition for treating bacterial infections comprising a therapeutically effective amount of a compound of claim 1, or a pharmaceutically acceptable salt, ester or prodrug thereof, in combination with a pharmaceutically acceptable carrier.

11. A method for treating bacterial infections comprising administering to an animal in need of such treatment a pharmaceutical composition comprising a therapeutically-effective amount of a compound of claim 1 or a pharmaceutically acceptable salt, ester or prodrug thereof.

12. A compound according to claim 1 which is selected from the group consisting of:

Compound of formula I: A is CHO, $R_1$ is H, Z is Ac and $Rp_1$ is H;

Compound of formula I: A is $CH_2OH$, $R_1$ is H, Z is Ac and $Rp_1$ is H;

Compound of formula I: A is $CH_2OCO$-[3-quinolyl], $R_1$ is H, Z is Ac and $Rp_1$ is H;

Compound of formula I: A is $CH_2OCO$-[4-quinolyl], $R_1$ is H, Z is Ac and $Rp_1$ is H;

Compound of formula I: A is CH=CH-phenyl, $R_1$ is H, Z is Ac and $Rp_1$ is H;

Compound of formula I: A is $CH_2NH$-benzyl, $R_1$ is H, Z is Ac and $Rp_1$ is H;

Compound of formula I: A is $CH_2NH$-allyl, $R_1$ is H, Z is Ac and $Rp_1$ is H;

Compound of formula II: A is CHO, $R_1$ is H, $R_2$ is H and $Rp_1$ is H;

Compound of formula II: A is CHO, $R_1$ is H, $R_2$ is benzoyl and $Rp_1$ is H;

Compound of formula II: A is $CH_2OH$, $R_1$ is H, $R_2$ is H and $Rp_1$ is H;

Compound of formula II: A is $CH_2OCO$-[3-quinolyl], $R_1$ is H, $R_2$ is H and $Rp_1$ is H;

Compound of formula II: A is $CH_2OCO$-[3-quinolyl], $R_1$ is H, $R_2$ is benzoyl and $Rp_1$ is H;

Compound of formula II: A is $CH_2OCO$-[4-quinolyl], $R_1$ is H, $R_2$ is H and $Rp_1$ is H;

Compound of formula II: A is CH=CH-phenyl, $R_1$ is H, $R_2$ is H and $Rp_1$ is H;

Compound of formula II: A is $CH_2NH$-benzyl, $R_1$ is H, $R_2$ is H and $Rp_1$ is H;

Compound of formula II: A is $CH_2NH$-benzyl, $R_1$ is H, $R_2$ is benzoyl and $Rp_1$ is H;

Compound of formula II: A is $CH_2NH$-allyl, $R_1$ is H, $R_2$ is H and $Rp_1$ is H;

Compound of formula III: A is CHO, B is H, C is H, D is H, $R_1$ is H, Z is Ac and $Rp_1$ is H;

Compound of formula III: A is CHO, B and D taken together are —O—, C is H, $R_1$ is H, Z is Ac and $Rp_1$ is H;

Compound of formula III: A is CHO, B and C taken together are =O, D is H, $R_1$ is H, Z is Ac and $Rp_1$ is H;

Compound of formula III: A is CHO, B is OH, D is OH, C is H, $R_1$ is H, Z is Ac and $Rp_1$ is H;

Compound of formula III: A is $CH_2OH$, B is H, C is H, D is H, $R_1$ is H, Z is Ac and $Rp_1$ is H;

Compound of formula III: A is $CH_2OH$, B and D taken together are —O—, C is H, $R_1$ is H, Z is Ac and $Rp_1$ is H;

Compound of formula III: A is $CH_2OH$, B and C taken together are =O, D is H, $R_1$ is H, Z is Ac and $Rp_1$ is H;

Compound of formula III: A is $CH_2OH$, B is OH, D is OH, C is H, $R_1$ is H, Z is Ac and $Rp_1$ is H;

Compound of formula III: A is $CH_2OCO$-[3-quinolyl], B is H, C is H, D is H, $R_1$ is H, Z is Ac and $Rp_1$ is H;

Compound of formula III: A is $CH_2OCO$-[3-quinolyl], B and D taken together are —O—, C is H, $R_1$ is H, Z is Ac and $Rp_1$ is H;

Compound of formula III: A is $CH_2OCO$-[3-quinolyl], B and C taken together are =O, D is H, $R_1$ is H, Z is Ac and $Rp_1$ is H;

Compound of formula III: A is $CH_2OCO$-[3-quinolyl], B is OH, D is OH, C=H, $R_1$ is H, Z is Ac and $Rp_1$ is H;

Compound of formula III: A is $CH_2OCO$-[4-quinolyl], B is H, C is H, D is H, $R_1$ is H, Z is Ac and $Rp_1$ is H;

Compound of formula III: A is $CH_2OCO$-[4-quinolyl], B and D taken together are —O—, C is H, $R_1$ is H, Z is Ac and $Rp_1$ is H;

Compound of formula III: A is $CH_2OCO$-[4-quinolyl], B and C taken together are =O, D is H, $R_1$ is H, Z is Ac and $Rp_1$ is H;

Compound of formula III: A is $CH_2OCO$-[4-quinolyl], B is OH, D is OH, C is H, $R_1$ is H, Z is Ac and $Rp_1$ is H;

Compound of formula III: A is CH=CH-phenyl, B is H, C is H, D is H, $R_1$ is H, Z is Ac and $Rp_1$ is H;

Compound of formula III: A is $CH_2NH$-benzyl, B is H, C is H, D is H, $R_1$ is H, Z is Ac and $Rp_1$ is H;

Compound of formula III: A is $CH_2NH$-benzyl, B and D taken together are —O—, C is H, $R_1$ is H, Z is Ac and $Rp_1$ is H;

Compound of formula III: A is $CH_2NH$-benzyl, B and C taken together are =O, D is H, $R_1$ is H, Z is Ac and $Rp_1$ is H;

Compound of formula III: A is $CH_2NH$-benzyl, B is OH, D is OH, C is H, $R_1$ is H, Z is Ac and $Rp_1$ is H;

Compound of formula III: A is $CH_2NH$-allyl, B is H, C is H, D is H, $R_1$ is H, Z is Ac and $Rp_1$ is H;

Compound of formula III: A is $CH_2NH$-allyl, B and D taken together are —O—, C is H, $R_1$ is H, Z is Ac and $Rp_1$ is H;

Compound of formula III: A is $CH_2NH$-allyl, B and C taken together are =O, D is H, $R_1$ is H, Z is Ac and $Rp_1$ is H;

Compound of formula III: A is $CH_2NH$-allyl, B is OH, D is OH, C is H, $R_1$ is H, Z is Ac and $Rp_1$ is H;

Compound of formula IV: A is CHO, B is H, C is H, D is H, $R_1$ is H, $R_2$ is H and $Rp_1$ is H;

Compound of formula IV: A is CHO, B and D taken together are —O—, C is H, $R_1$ is H, $R_2$ is H and $Rp_1$ is H;

Compound of formula IV: A is CHO, B and C taken together are =O, D is H, $R_1$ is H, $R_2$ is H and $Rp_1$ is H;

Compound of formula IV: A is CHO, B is OH, D is OH, C is H, $R_1$ is H, $R_2$ is H and $Rp_1$ is H;

Compound of formula IV: A is $CH_2OH$, B is H, C is H, D is H, $R_1$ is H, $R_2$ is H and $Rp_1$ is H;

Compound of formula IV: A is $CH_2OH$, B and D taken together are —O—, C is H, $R_1$ is H, $R_2$ is H and $Rp_1$ is H;

Compound of formula IV: A is $CH_2OH$, B and C taken together are =O, D is H, $R_1$ is H, $R_2$ is H and $Rp_1$ is H;

Compound of formula IV: A is $CH_2OH$, B is OH, D is OH, C is H, $R_1$ is H, $R_2$ is H and $Rp_1$ is H;

Compound of formula IV: A is $CH_2OCO$-[3-quinolyl], B is H, C is H, D is H, $R_1$ is H, $R_2$ is H and $Rp_1$ is H;

Compound of formula IV: A is $CH_2OCO$-[3-quinolyl], B and D taken together are —O—, C is H, $R_1$ is H, $R_2$ is H and $Rp_1$ is H;

Compound of formula IV: A is $CH_2OCO$-[3-quinolyl], B and C taken together are =O, D is H, R1 is H, $R_2$ is H and $Rp_1$ is H;

Compound of formula IV: A is $CH_2OCO$-[3-quinolyl], B is OH, D is OH, C is H, $R_1$ is H, $R_2$ is H and $Rp_1$ is H;

Compound of Formula IV: A is $CH_2OCO$-[4-quinolyl], B is H, C is H, D is H, $R_1$ is H, $R_2$ is H and $Rp_1$ is H;

Compound of Formula IV: A is $CH_2OCO$-[4-quinolyl], B and D taken together are —O—, C is H, $R_1$ is H, $R_2$ is H and $Rp_1$ is H;

Compound of Formula IV: A is $CH_2OCO$-[4-quinolyl], B and C taken together are =O, D is H, $R_1$ is H, $R_2$ is H and $Rp_1$ is H;

Compound of Formula IV: A is $CH_2OCO$-[4-quinolyl], B is OH, D is OH, C is H, $R_1$ is H, $R_2$ is H and $Rp_1$ is H;

Compound of formula IV: A is CH=CH-phenyl, B is H, C is H, D is H, $R_1$ is H, $R_2$ is H and $Rp_1$ is H;

Compound of Formula IV: A is $CH_2NH$-benzyl, B is H, C is H, D is H, $R_1$ is H, $R_2$ is H and $Rp_1$ is H;

Compound of Formula IV: A is $CH_2NH$-benzyl, B and D taken together are —O—, C is H, $R_1$ is H, $R_2$ is H and $Rp_1$ is H;

Compound of Formula IV: A is $CH_2NH$-benzyl, B and C taken together are O, D is H, $R_1$ is H, $R_2$ is H and $Rp_1$ is H;

Compound of Formula IV: A is $CH_2NH$-benzyl, B is OH, C is OH, D is H, $R_1$ is H, $R_2$ is H and $Rp_1$ is H;

Compound of Formula IV: A is $CH_2NH$-allyl, B is H, C is H, D is H, $R_1$ is H, $R_2$ is H and $Rp_1$ is H;

Compound of Formula IV: A is $CH_2NH$-allyl, B and D taken together are —O—, C is H, $R_1$ is H, $R_2$ is H and $Rp_1$ is H;

Compound of Formula IV: A is $CH_2NH$-allyl, B and C taken together are =O, D is H, $R_1$ is H, $R_2$ is H and $Rp_1$ is H; and Compound of Formula IV: A is $CH_2NH$-allyl, B is OH, D is OH, C is H, $R_1$ is H, $R_2$ is H and $Rp_1$ is H.

* * * * *